` `United States Patent [19]
Saltiel

[11] Patent Number: 4,906,468
[45] Date of Patent: Mar. 6, 1990

[54] INSULIN ACTIVITY MESSENGERS, THEIR ANTIBODIES, AND THEREOF
[75] Inventor: Alan R. Saltiel, New York, N.Y.
[73] Assignee: The Rockefeller University, New York, N.Y.
[21] Appl. No.: 850,842
[22] Filed: Apr. 11, 1986
[51] Int. Cl.[4] .............................................. A61K 39/00
[52] U.S. Cl. ...................................... 424/85.8; 514/2; 514/3; 514/8; 514/7; 514/23; 536/18.7
[58] Field of Search ......................... 514/23, 2, 3, 8, 7; 536/18.7; 424/85.8

[56] References Cited
PUBLICATIONS

Jarett et al–Chem. Abst., vol. 97 (1982) p. 85761z.

Primary Examiner—Sam Rosen
Attorney, Agent, or Firm—Klauber & Jackson

[57] ABSTRACT

An insulin activity messenger material and its precursor material are disclosed which have been isolated from hapatic plasma membranes that have been incubated with an enzyme known as a phosphtidylinositol-specific phospholipase C. The messenger material comprises a carbohydrate-based compound that exhibits the ability to modulate the activity of the insulin-sensitive enzymes pyruvate dehydrogenase, adenylate cyclase, acetyl CoA carboxyase, and low Km cAMP phosphodiesterase, and thereby effectuate the activity of insulin on the cellular level. The precursor material comprises an inositol containing glycolipid capable of phosphodiesteratic cleavage by a phosphatidylinositol-specific phospholipase C. Numerous diagnostic and therapeutic utilities are proposed, and testing procedures, materials in kit form, antibodies, and pharmaceutical compositions are likewise set forth.

3 Claims, 15 Drawing Sheets

FIG. I

INSULIN ACTIVITY MESSENGERS, THEIR ANTIBODIES, AND THEREOF

RELATED PUBLICATIONS

The Applicant is an author or co-author of several articles directed to the general area of the subject matter of the present invention. (1) [Applicant is a co-author with S. Jacobs, M. Siegel, and P. Cuatrecasas] "Insulin Stimulates The Release From Liver Plasma Membranes Of a Chemical Modulator of Pyruvate Dehydrogenase" BIOCHEM. BIOPHYS RES. COMM 102 (3) at 1041–1047, (Oct. 1981); (2) [Applicant, M. Siegel, S. Jacobs and P. Cuatrecasas] "Putative Mediators of Insulin Action: Regulation of Pyruvate Dehydrogenase and Adenylate Cyclase Activities", PROC. NATL. ACAD. SCI. U.S.A., 79: 3513–3517 (1982); (3) [Applicant, A. Doble, S. Jacobs and Cuatrecasas] "Putative Mediators of Insulin Action Regulate Hepatic Acetyl CoA Carboxylase Activity", BIOCHEM. BIOPHYS. RES. COMM., 110 (3) at 789–795, (Feb., 1983); (4) [Applicant is sole author] "Preparation and Characterization of Putative Insulin Mediators From Liver", METHODS DIAB. RES., Vol. I, Laboratory Methods, Part B, Pages 73–79 (1984), J. Larner and S. Pohl, Eds., John Wiley & Sons Inc; (5) [Applicant is a co-author with J. A. Gox and P. Cuatrecasas] "Insulin stimulates the Hydrolysis of a novel Membrane Glycolipid Causing the Generation of cAMP Phosphodiesterase Modulators", (not yet submitted for publication); and (6) [Applicant is co-author with P. Cuatrecasas], "Insulin Stimulates the Generation of cAMP Phosphodiesterase Modulators from Hepatic Plasma Membranes", (not yet submitted for publication). All of the above listed articles are incorporated herein by reference.

The research leading to the present invention was funded in part by a grant from the National Institutes of Health.

BACKGROUND OF THE INVENTION

The present invention is generally directed to materials and associated methods for the analysis and treatment of diabetic disorders, and in particular, is concerned with the identification, analysis and application of materials that may participate in the transmission and effectuation of insulin action that averts the occurrence of the diabetic condition.

For some time, diabetic research has focused on the action of insulin at the cellular level, and in particular, has determined that insulin action may take place by the generation of intracellular mediators which modulate certain key enzymes. Thus, it has been believed for some time that insulin action at the cellular level is not direct but rather occurs through the stimulation by insulin of its cellular receptors which in turn, cause the generation and dispatch of hitherto chemically undefined substances which stimulate certain key enzyme activities.

Thus, while the diabetic condition is largely attributed to an inability of the patient to synthesize sufficient insulin, a particular variety of diabetes known as Type II adult-onset diabetes is recognized, wherein the patient is capable of synthesizing sufficient quantities of insulin and likewise possesses sufficient cellular receptors. however, the activities of insulin are not carried out. Applicant and the co-workers identified in Publication Nos. 1–4 above, have conducted extensive investigations of the cellular environment, in particular with rat liver fractions, and determined that such mediators or messengers exist that appear to modulate the activities of certain key enzymes such as pyruvate dehydrogenase, adenylate cyclase and acetyl CoA carboxylase. Despite the extensive knowledge gained from the review of the results of these investigations, there still existed no knowledge as to the actual mechanisms on the cellular level that were involved in the generation of the messenger material, nor was there a suggestion as to the chemical structure and correspondingly, the identity and number of constituents of such messenger material.

In Publication No. 4, the present inventor speculated that two materials may exist, the first being a stimulator and the second an inhibitor. Notwithstanding efforts to characterize the molecular weight of these materials and to determine within some general scope the activity of these materials, the exact identity of the materials has remained unknown as has their origin and action.

The present application is therefore directed to the identification of messenger material as to its structure, origin and action, and to corresponding diagnostic and therapeutic applications to which the messenger material may be put.

SUMMARY OF THE INVENTION

In accordance with the present invention a messenger material for insulin activity has been isolated which comprises at least one carbohydrate-based compound capable of modulating the activity of the enzymes pyruvate dehydrogenase, adenylate cyclase, acetyl CoA carboxylase and low Km cAMP phosphodiesterase from fat and liver cells, and thereby effectuating the activity of insulin on the cellular level. In one embodiment the messenger material is derivable from hepatic tissue, and in particular may be derived from hepatic plasma membranes that have been incubated with an enzyme known as a phosphatidylinositol-specific phospholipase C. Alternately, this enzyme may be incubated with an extract, derived from a culture of an insulin-responsive murine myocyte cell line, identified as the cell line $BC_3Hl$, which becomes responsive to insulin upon differentiation following attainment of confluence.

More particularly, two carbohydrate-containing compounds have been identified in accordance with the present invention that appear to act as messengers. These compounds share certain common characteristics, among them a non-proteinoid structure, a net negative charge believed to be attributable to the presence of a charged substituent such as phosphate or sulphate, relative polarity, and the presence of glucosamine. More specifically, the messenger compounds are believed to comprise, respectively, a 1,2 cyclic phosphodiester inositol derivative, and a 1- or 2-phosphomonoester inositol derivative, each in respective combination or mixture with glucosamine, and other carbohydrate constituents.

The messenger material of the present invention has been found to be produced by the phosphodiesteratic cleavage of an inositol-containing glycolipid precursor material, the discovery of such precursor material also comprising an aspect of the present invention. Accordingly, the precursor material of the present invention is isolatable from a substrate such as hepatic cells and the insulin-responsive murine myocyte cell line, referred to above. The precursor material identified in accordance with the present invention has been determined to comprise a glycolipid containing the carbohydrates inositol and glucosamine, as well as a diacylglycerol. Further elucidation of the precursor material is presently in progress.

The discovery of the insulin activity messenger material and its precursor material offers the opportunity to further investigate the exact mechanism of the action of insulin and possibly other hormones, and to formulate appropriate therapies in the instance where such action is abnormal and diabetic disorders of the type mentioned earlier herein occur. Thus, the messenger material and stable analogs thereof may be pharmacologically useful in the treatment of such disorders. Moreover, the biosynthesis, generation, activities, degradation and processing of both the messenger material and the precursor material may be the subject of various diagnostic procedures, and accordingly, both materials may be appropriately prepared with detectable labels for use in both in vitro and possibly in vivo diagnostic procedures. For example, radio labeled quantities of either material may be introduced into sample fluids and cellular systems on an in vitro basis and observed to determine the course of activity and movement.

The invention further includes a method for detecting hormonal abnormalities by measurement of the activities affected by the present messenger material or its precursor. In particular, hormones or hormonal conditions could be identified and detected by the supression or other alterations in the activity of the messenger material upon the target insulin-sensitive enzymes that it affects. In this method, cells derived for example, from the insulin-sensitive murine myocyte cell line could be innoculated with the messenger material or its precursor material as a control, while parallel cellular samples could be innoculated with the same quantity of messenger material or precursor material and one or more agents suspected of adversely affecting insulin action. All samples could thereafter be incubated in accordance with the methods described above, and thereafter subjected to the sequence of separation techniques also defined, whereupon testing of the resulting isolates derived from the control and unknown samples could be compared to determine whether the material is adversely affected by observing the affect if any, on the listed target enzymes.

In similar fashion, an assay system for screening of potential drugs effective to treat diabetic and other possible hormonal abnormalities related to messenger activities, may be prepared. In one instance, the test drug could be administered to an untreated murine myocyte sample to determine its effect upon the production of the messenger material. In an alternate procedure, the messenger material may be introduced into the cellular test system, and the prospective drug may then be introduced to the resulting cell culture and the culture may thereafter be examined to observe any changes in the activity of the modulator material, either from the addition of the prospective drug alone, or the effect of added quantities of the known modulator material.

The present invention also relates to a method for detecting the presence or onset of diabetic pathology in mammals, by measuring the activity and presence of the messenger material of the present invention. Pathological states may result from hormonal insensitivities in which cells are deficient in the biosynthesis of the precursor material, the enzyme responsible for hydrolysis of the precursor, or coupling of the hormone receptor to activation of the enzyme. Alternatively, the hormone-stimulated generation of messenger may be unaltered, but the activity of the messenger may be diminished by enzymatic modification or degradation. Thus, the generation, activity or metabolism of the messenger material may be followed directly by the assay techniques discussed later on, through the use of an appropriately labeled quantity of the material. Alternately, the messenger can be used to raise binding partners or antibodies that could in turn, be labeled and introduced into an appropriate medium to test for the presence of messenger material therein, and to thereby assess the pathological state of the host from which the medium was drawn. Thus, both the messenger material and any antibodies that may be raised thereto, are capable of use in connection with various diagnostic techniques, including immunoassays, such as a radioimmunoassay, using for example, an antibody to the messenger material that has been labeled by either radioactive addition, reduction with sodium borohydride, or radioiodination.

In an immunoassay, a control quantity of the messenger material, its antibody, or the like may be prepared and labeled with an enzyme, a specific binding partner and/or a radioactive element, and may then be introduced into a plasma membrane cellular sample of a mammal believed to be suffering from diabetic disorder. After the labeled material or its binding partner(s) has had an opportunity to react with receptor sites within the sample, the resulting mass may be examined by known detecting techniques, which may vary with the nature of the label attached.

In the instance where a radioactive label, such as the isotopes $^{14}C$, $^{131}I$, $^{3}H$, $^{125}I$ and $^{35}S$ are used, known currently available counting procedures may be utilized. In the instance where the label is an enzyme, detection may be accomplished by any of the presently utilized colorimetric, spectrophotometric, fluorospectrophotometric or gasometric techniques known in the art.

The present invention includes an assay system which may be prepared in the form of a test kit for the quantitative analysis of the extent of messenger material activity. The system or test kit may comprise a labeled component prepared by one of the radioactive and/or enzymatic techniques discussed herein, coupling a label to the messenger material; and one or more additional immunochemical reagents, at least one of which is a free or immobilized ligand, capable either of binding with the labeled component, its binding partner, one of the components to be determined or their binding partner(s).

Furthermore, the invention includes an assay system to quantitate the possible degradative activity present in tissues, cells or extacts thereof in patients with hormonal disorders. This system or test kit may comprise a labeled compound prepared as detailed above, with one or more chemical or immunological reagents or instructions on chromatographic degradative or modified products of the messenger substance.

In a further embodiment, the present invention relates to certain therapeutic methods associated with the prevention of the development, or the arrest of diabetic disorders in mammals, by the administration of physiologically effective amounts of either the precursor material or the messenger material, or analogs synthesized according to information derived from the structure activity experiments of the present invention. Thus, in the instance where type II adult-onset diabetes is present, the condition of the patient may be monitored and appropriate of the materials of the present invention may be administered on a periodic basis to supplement the insulin activity system of the patient and to thereby counteract the adverse effects of a messenger or precursor deficiency. Correspondingly, in instances where insulin activity is excessive, appropriate antibodies to the precursor material and messenger material may be developed and administered to inhibit the action of these materials and to thereby control the insulin activity system of the patient to correct any abnormalities thereof.

Accordingly, it is a principal object of the present invention to provide a method for the preparation of an insulin activity messenger material or analog that participates in effectuating insulin activity on the cellular level.

It is a further object of the present invention to provide a method for the preparation, identification and isolation of a precursor material for the insulin activity messenger material.

It is a further object of the present invention to provide a method and associated assay system for screening substances such as drugs, agents and the like, potentially effective in combating the adverse effects resulting from the lack of the insulin activity messenger material within the proper amounts required for normal cellular insulin activity.

It is a still further object of the present invention to provide a method for the treatment of mammals to avert the onset of diabetic disorder caused by the lack of the proper quantity and activity of the insulin activity messenger material of the present invention.

It is a still further object of the present invention to provide pharmaceutical compositions for use in therapeutic methods relating to the regulation of the quantity of the insulin activity messenger material.

Other objects and advantages will become apparent to those skilled in the art from a review of the ensuing description which proceeds with reference to the following illustrative drawings.

BC$_3$Hl cells were cultured at 37° C. in Dubelco's Minimal Essential Medium in the presence of 20% NU serum (Collaborative Research) on collagen coated 10 mm miniwells. Cells ($1 \times 10^6$/well) were preincubated with 10 $\mu$Ci A) [2,6$^3$H]myoinositol or B) [1,6$^3$H]glucosamine (New England Nuclear) for 20 hours in the presence of 20% Nu Serum. Insulin was added to cells in monolayer in serum free media at a final concentration of 10 nM. Reactions were terminated by removal of media and addition of 1 ml chloroform/methanol/IN HCl (200:100:1), followed by addition of 0.5 ml 10 mM formic acid. Organic and aqueous phases were separated by centrifugation at $500 \times g$ for 5 min.

The water soluble labeled products were purified by a modification of a previously described protocol for purification of cAMP phosphodiesterase (PDE) modulators. The aqueous phases were chromatographed on DEAE-Cellulose, eluted with 0.25 TEA-formate, pH 3.75. This fraction was eluted through a C-18 reversed phase sepak in the same buffer. Following lyophilization, the solution was eluted through Dowex 50WX-4 in 50 mM TEA-formate. pH 3.0. After exposure to activated charcoal, samples were chromatographed on an SAX HPLC column (Whatman), eluted with a linear, 15 minute gradient of 60% methanol (A) to 0.5 M TEA-formate, pH 3.75 (B) at 1 ml/minute. One ml fractions were counted. The two peaks of insulin stimulated radioactivity coeluted with similarly purified, myocyte derived PDE modulating activities.

Figure 8:
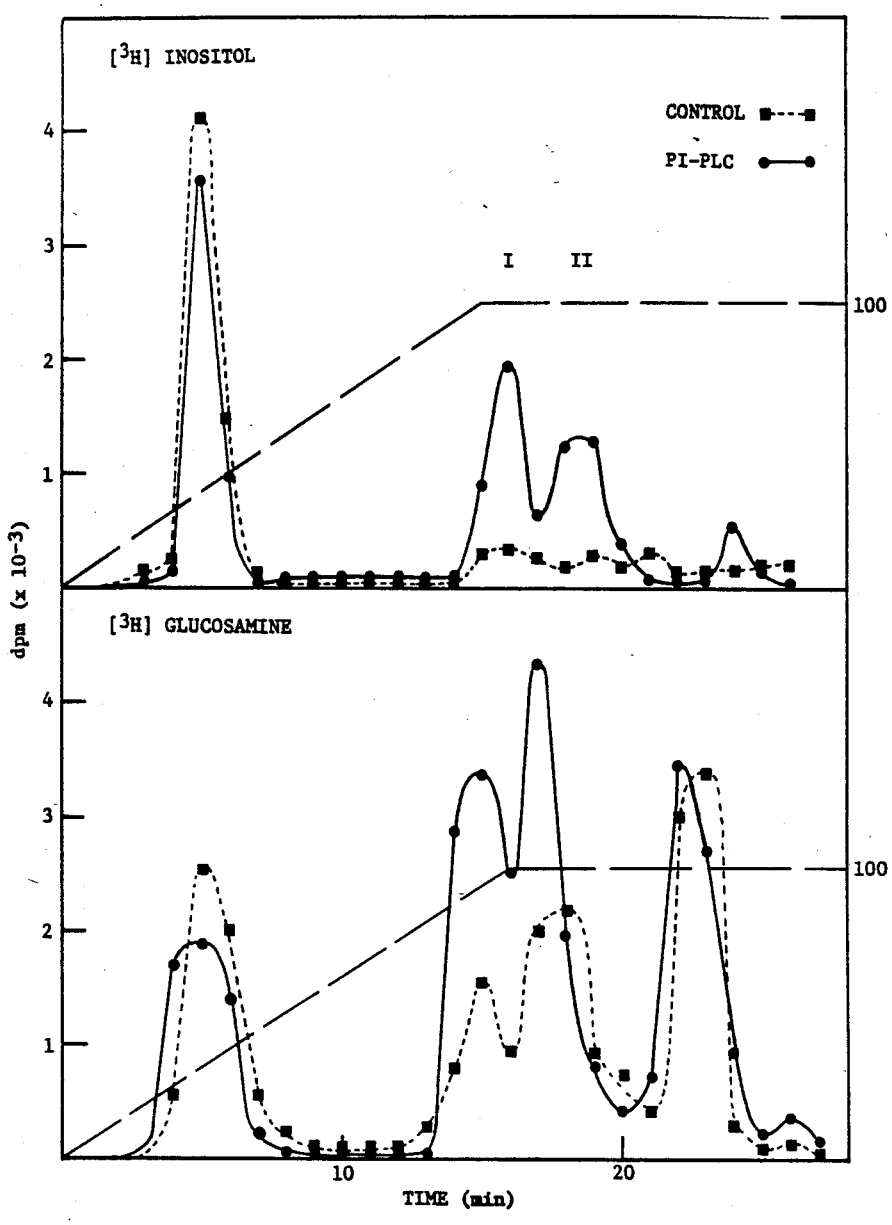

FIG. 8 - SAX HPLC of Radiolabeled Mediators Produced by PI-PLC.

Figure 7:
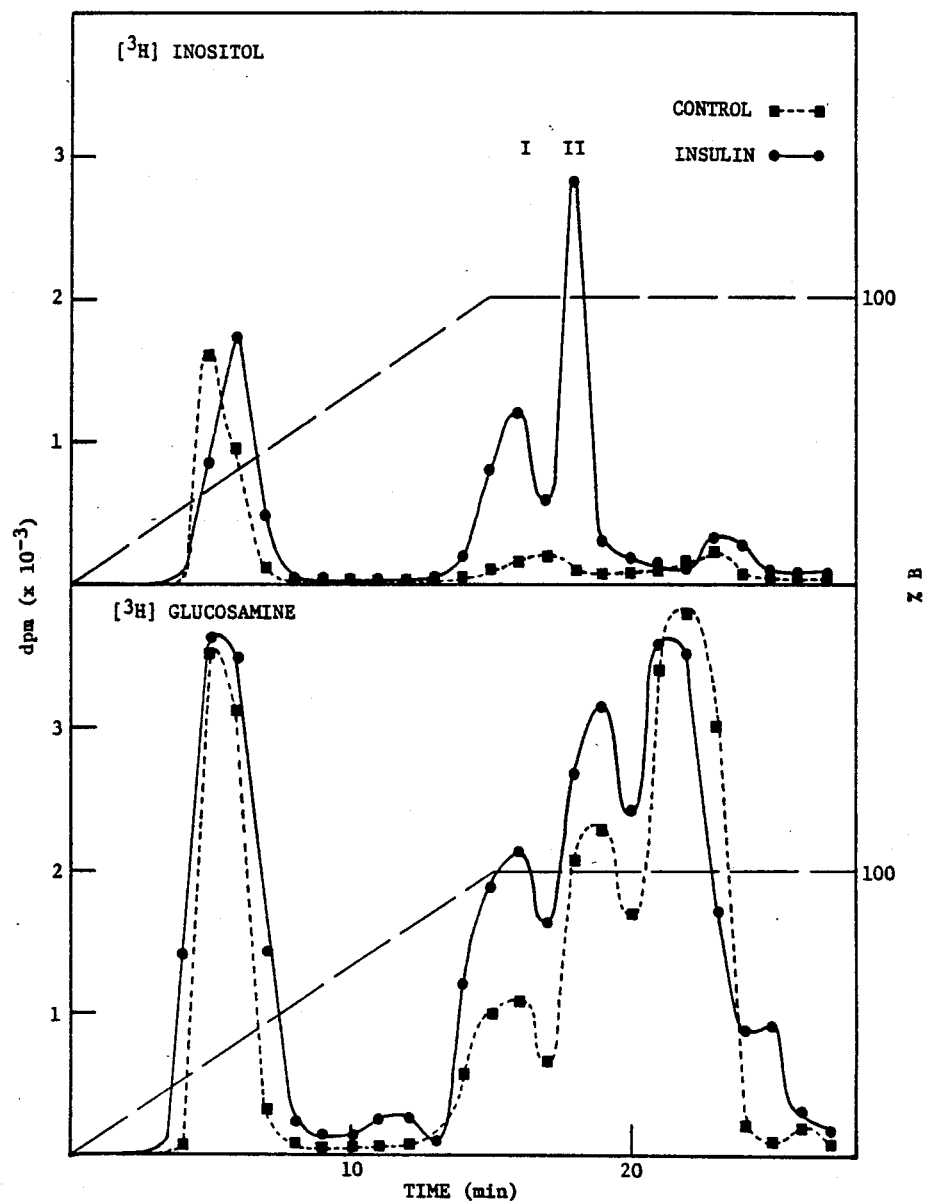
FIG. 7 - SAX HPLC of Radiolabeled Mediators from Insulin Treated Cells.

Cells were prelabeled as described in FIG. 7, extracted in chloroform/methanol/IN HCl (200:100:1) and centrifuged at $1000 \times g$ for 10 min. The supernatant was dried under $N_2$ and resuspended in 1 mil of 50 mM ammonium bicarbonate, pH 7.4. These solutions were treated with 0.1 $\mu$g/ml PI-PLC from S. aureus for 30 min. at 37° C. Reactions were terminated by reextraction with 1 ml of chloroform/methanol/IN HCl (200:100:1) and aqueous and organic phases separated. The aqueous phases were then purified as described in FIG. 7 and chromatographed on SAX HPLC column, eluted as described.

Figure 9:
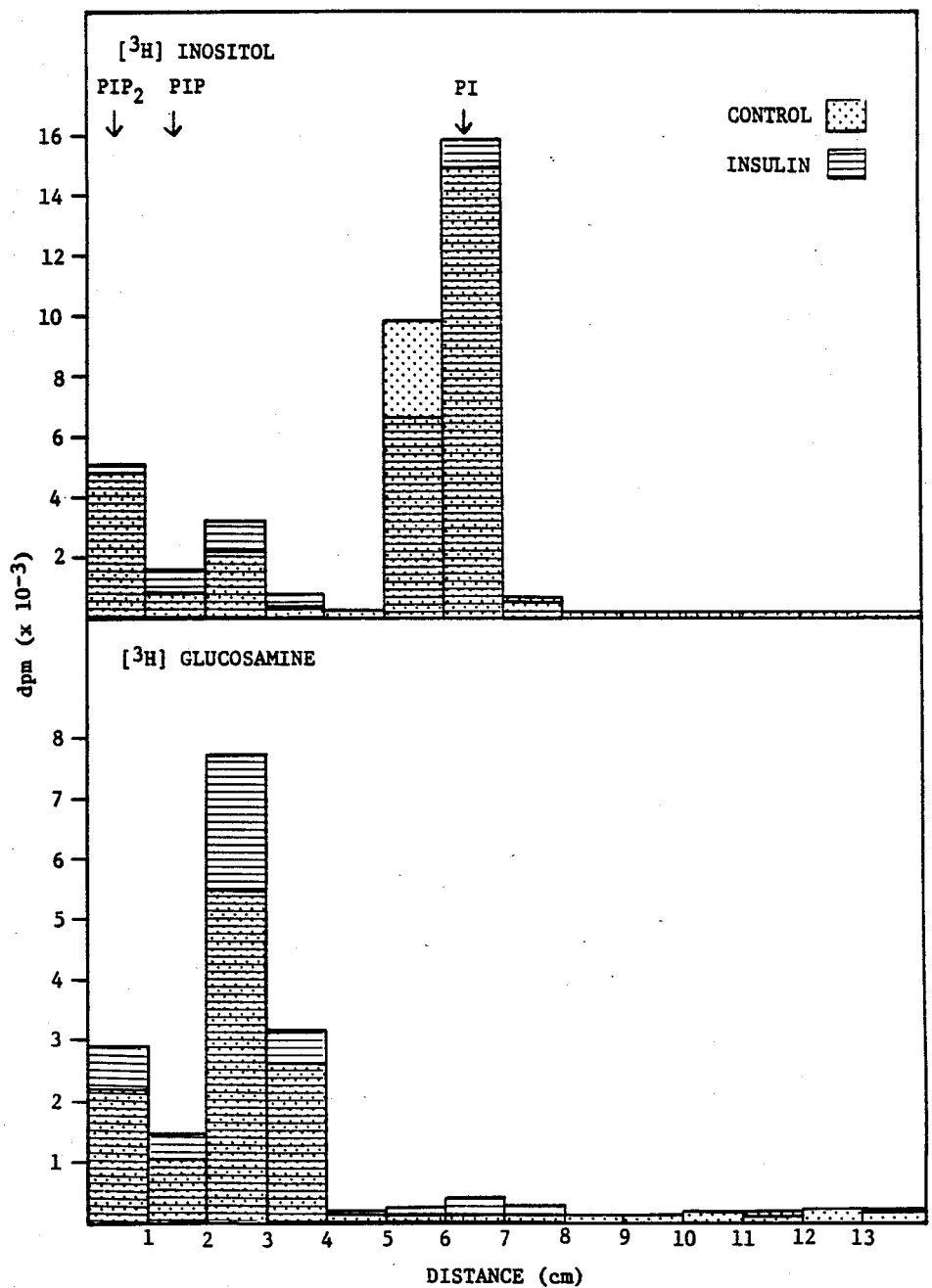

FIG. 9 - Thin Layer Chromatography of the Radiolabeled Precursor from Insulin Treated Cells.

(A) [$^3$H]inositol and (B) [$^3$H]glucosamine labeled cells were treated with or without 10 nM insulin. Following extraction and phase separation, the organic phase were dried under $N_2$, resuspended in chloroform/methanol/$H_2O$ (9:7:2); and spotted on oxalate impregnated Silica gel G plates. These were twice developed in chloroform/acetone/methanol/glacial acetic acid/$H_2O$ (10:4:2:2:1). One cm regions were scraped and radioactivity determined by scintillation counting. Phosphoinositides were identified by iodine staining of standards.

Figure 10:
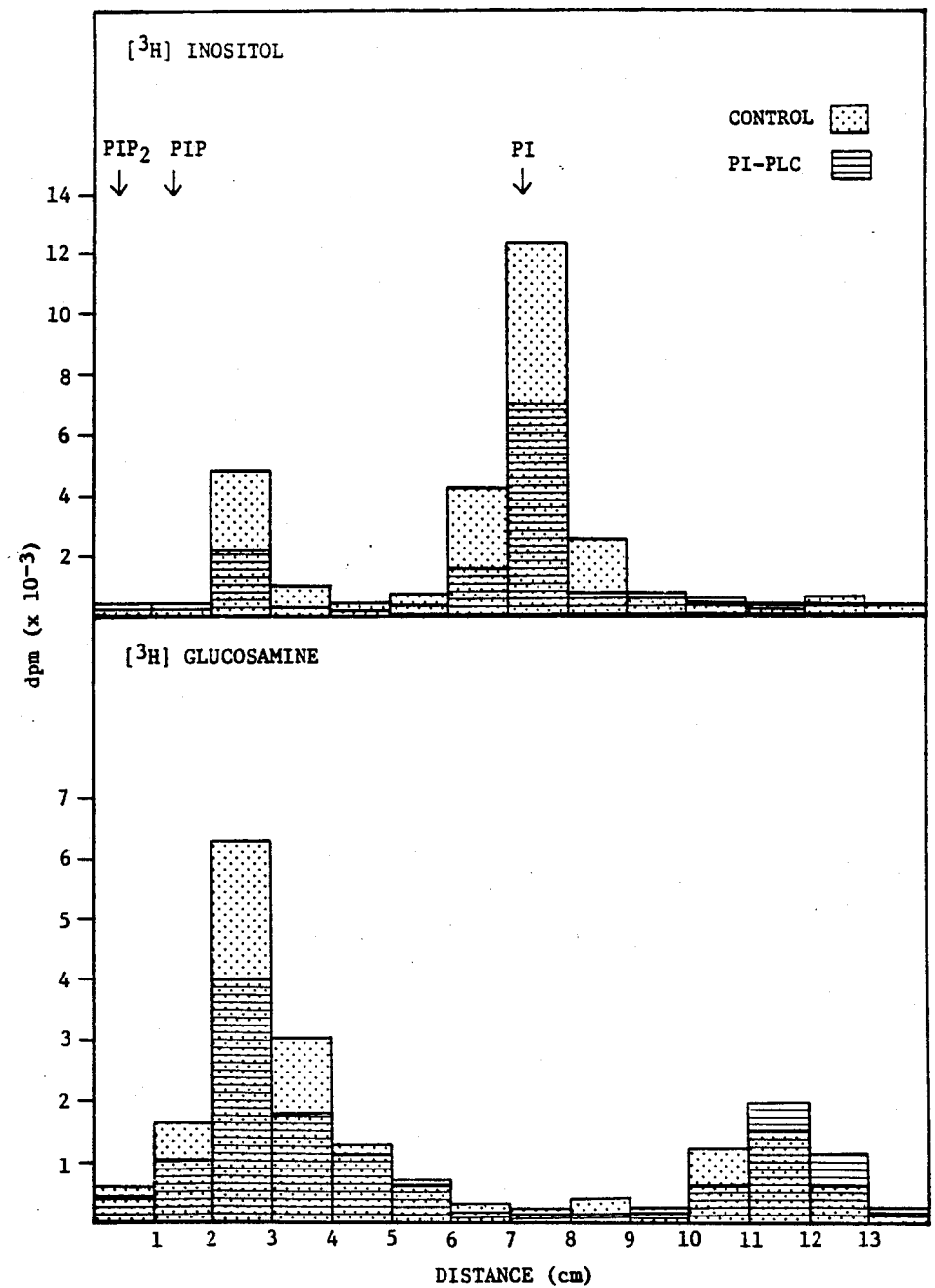

FIG. 10 - Thin Layer Chromatography of the Radiolabeled Precursor After PI-PLC Treatment.

Cells were labeled, extracted treated with or without PI-PLC and reextracted as described in FIG. 8. Organic phases were chromatographed on thin layer plates as detailed in FIG. 9.

Figure 11:
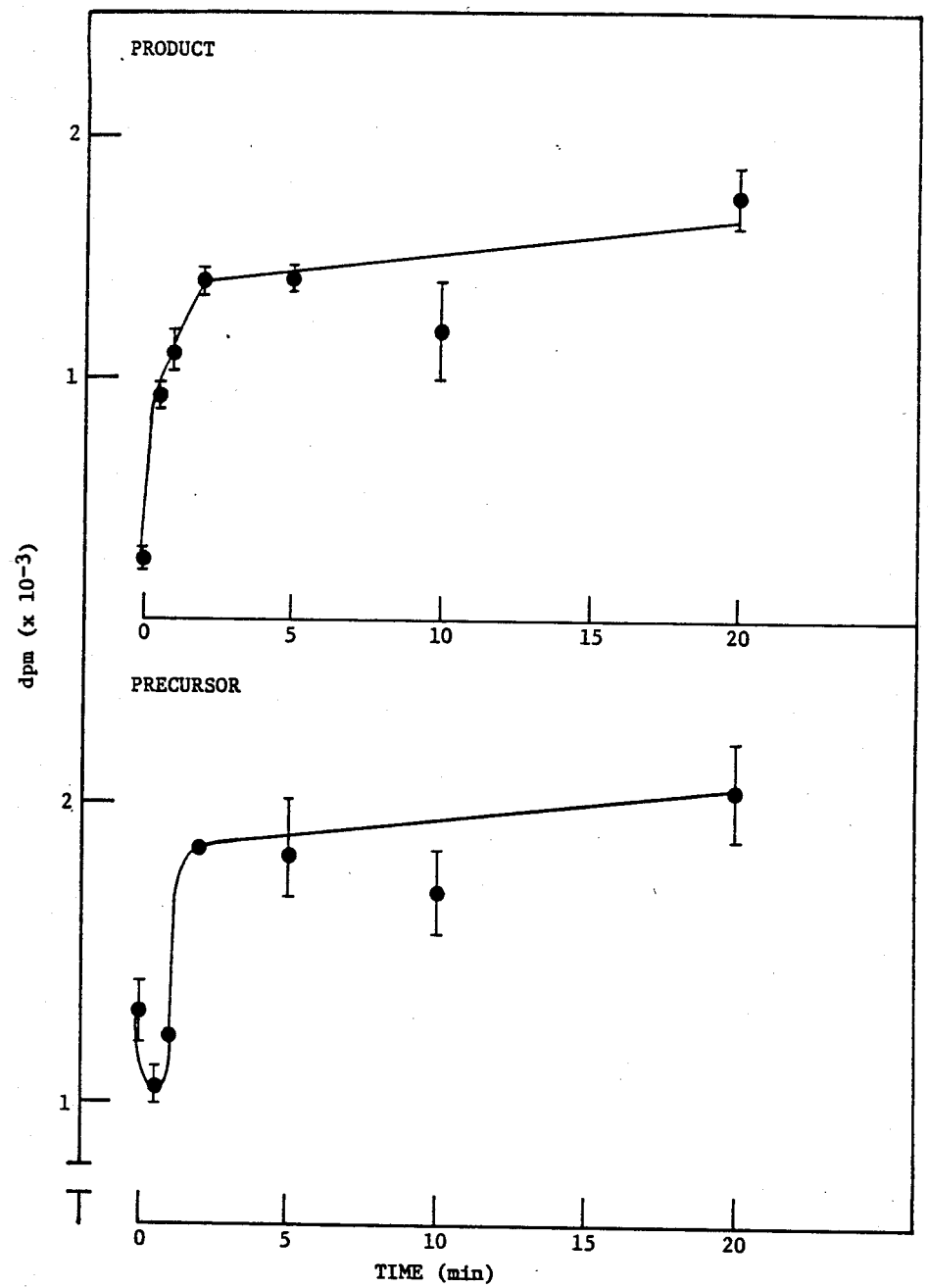

FIG. 11 - Time Course of Precursor Hydrolysis by Insulin.

Cells prelabeled with [$^3$H]inositol were treated with 10 nM insulin for the designated intervals. Cells were extracted and phase separated as detailed in FIG. 7. Aqueous phases were chromatographed up to and including the SAX HPLC step (upper panel). Results reflect counts from a combination of Peaks I and II. The ratio of counts in these peaks were unchanged over the time course. The precursor residing in the organic phases was identified by the peak on TLC with an $R_f=0.22$, corresponding to the species depleted by PI-PLC (FIG. 10).

Figure 12:
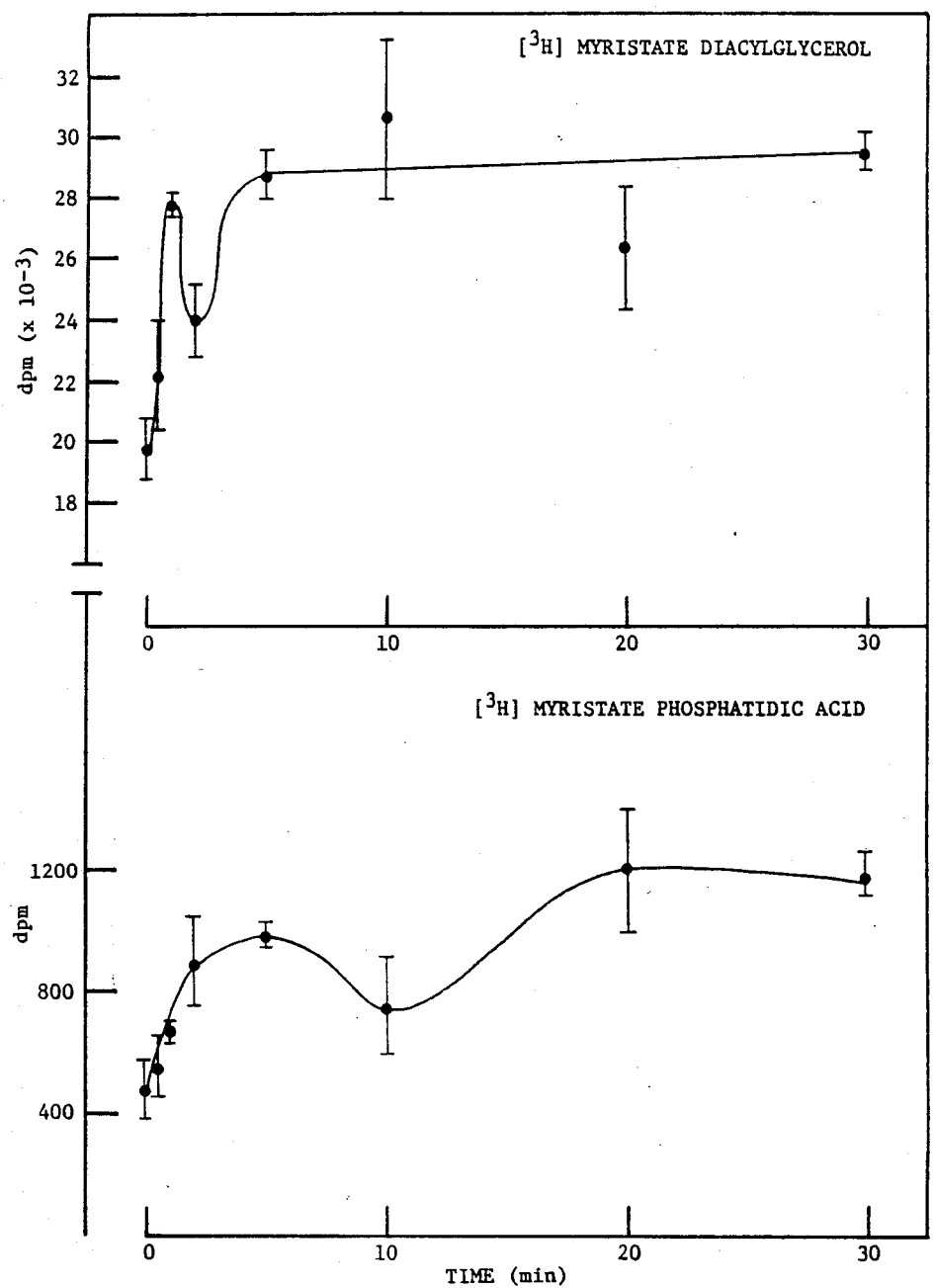

FIG. 12 - Time Course of Diacylglycerol and Phosphatidic Acid Production in Response to Insulin.

Myocytes were incubated for 20 hrs. in serum free DMEM with [9,10$^3$H] myristic acid (New England Nuclear), complexed 1:1 to bovine serum albumin. Insulin was added to cells in fresh media for the designated intervals, and reactions were stopped by removal of media and addition of 1 ml chloroform/methanol/IN HCl (200:100:1). 0.6 ml $H_2O$ was added and upper aqueous phases were discarded following centrifugation at 500×g for 5 minutes. The lower, organic phases were dried under $N_2$ and resuspended in 1 ml diethyl ether followed by addition of 1 ml mM formic acid. The upper ether phase was aspirated and the lower phase reextracted with 1 ml diethyl ether. The combined ether phases, containing diacylglycerol, were dried under $N_2$, resuspended in chloroform and spotted on silica gel G plates which were preactivated at 60° C. for 1 hr. Plates were twice developed in petroleum ether/diethyl ether/glacia acetic acid (70:30:2). Five μg of unlabeled dimyristoylglycerol were added to each sample. Spots were visualized by iodine staining. To the lower aqueous phases from the ether extraction were added 1 ml of chloroform/methanol (2:1). Following centrifugation, the resulting upper aqueous phases were discarded and the lower organic phases dried under $N_2$, resuspended in chloroform/methanol/$H_2O$ (9:7:2) and spotted on "soft plus" silica gel plates. These were developed in chloroform/pyridine/70% formic acid (50:30:7), and phosphatidic acid was identified by an iodine stained standard. Lipids were scraped and radioactivity determined in a liquid scintillation counter.

Figure 13:
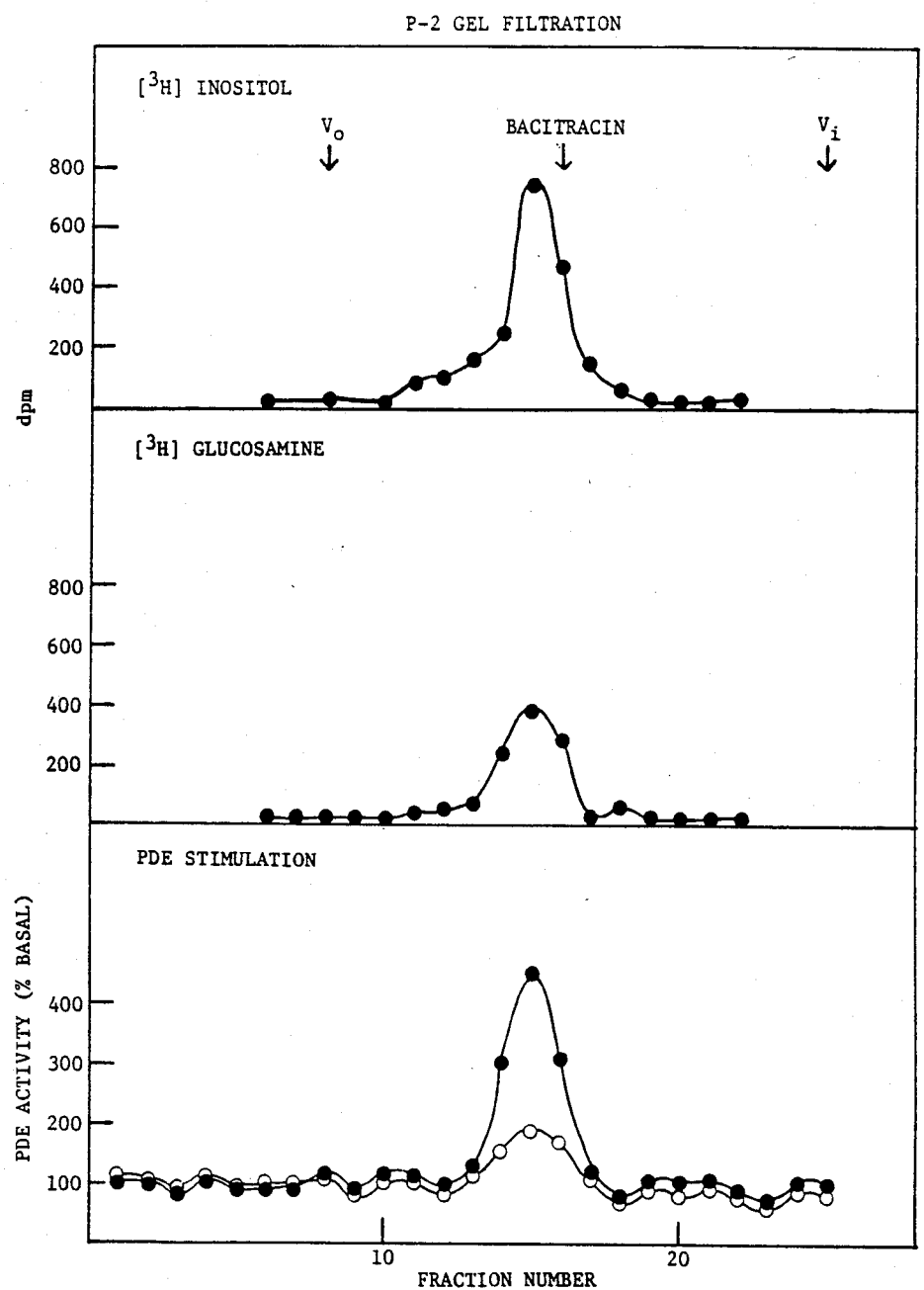

FIG. 13 - Gel Filtration of Radioactive and Bioactive Mediators.

(A) [$^3$H]Inositol and (B) [$^3$H]glycosamine labeled substances from Peak I from SAX HPLC were chromatographed on a 45 ml P-2 gel filtration column in 50 mM formic acid. Unlabeled cells were extracted by an identical procedure, and chromatographed on an SAX HPLC column, as described in FIG. 7. Active fractions eluting in Peaks I and II were identified by stimulation of the low km cAMP phosphodiesterase (PDE) activity. This was assayed in adipocyte particulate fractions.

Bioactivity in Peak I was chromatographed on the P-2 column (panel C). Fractions were collected and counted or assayed for PDE modulating activity. Radioactivity residing in Peak II from SAX exhibited identical elution volumes on this column (not shown).

Figure 14:
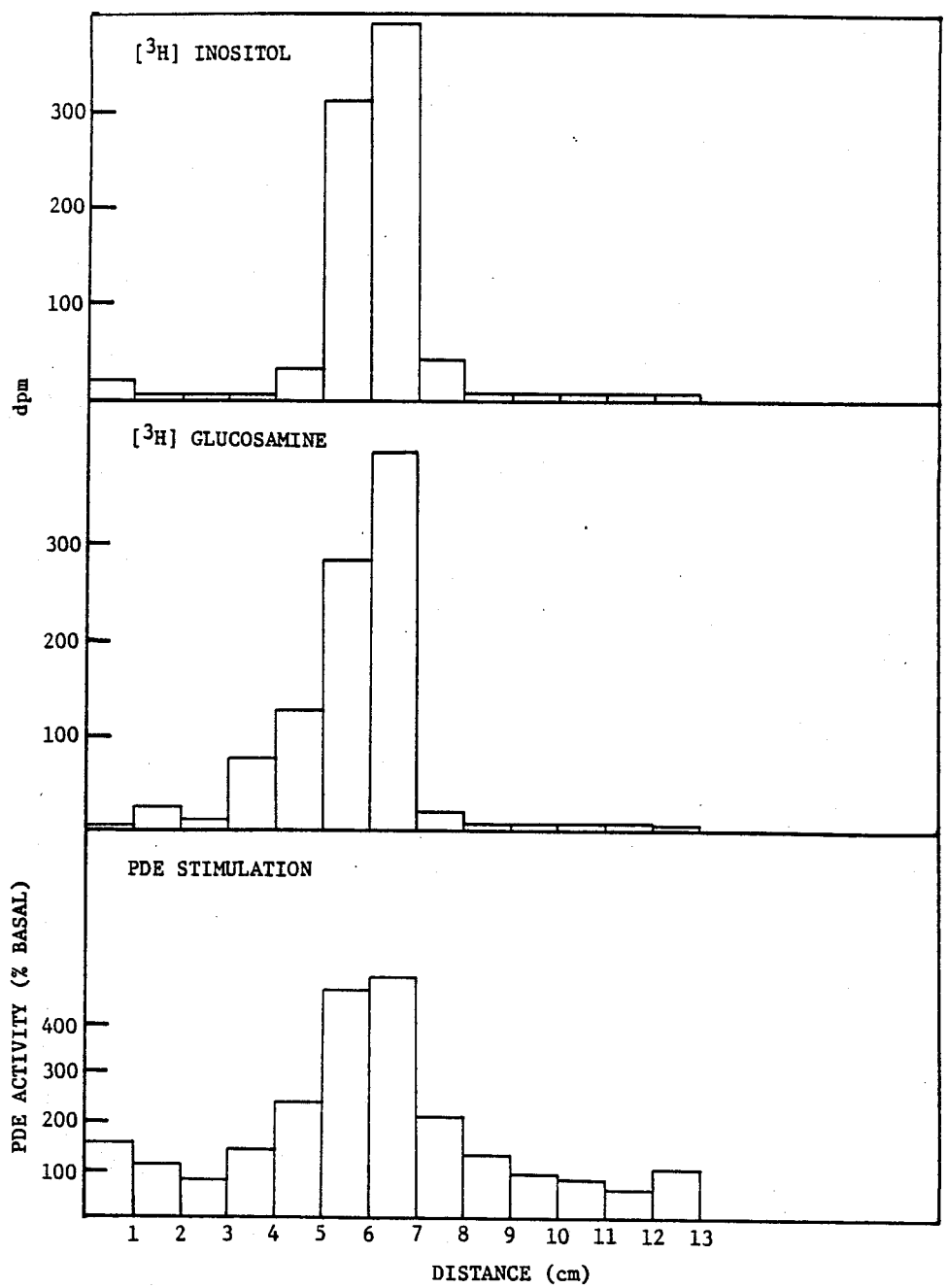

FIG. 14 - High Voltage Electrophoresis of Radioactive and Bioactive Mediators.

After gel filtration, purified radioactive and bioactive fractions residing in SAX Peak I were subject to high voltage electrophoresis on cellulose coated thin layer plates at 500 volts for 1 hr. The pH of the running buffer was 3.5 (pyridine/glacial acetic acid/$H_2$ (1:10:189). One cm regions were scraped an eluted with 50% methanol of 10 mM formic acid. [$^3$H]Inositol and [$^3$H]glucosamine labeled samples were counted. Bioactive samples were assayed for PDE modulating activity as detailed in FIG. 13. Radioactive and bioactive samples exhibited identical migrations when electrophoresed at pH 1.9 (88% formic acid/glacial acetic acid/$H_2O$ (50:56:1794). Radioactivity and bioactivity residing in Peak II similarly migrated slightly farther from the origin at both pH 1.9 and 3.5, as described above.

Figure 15:
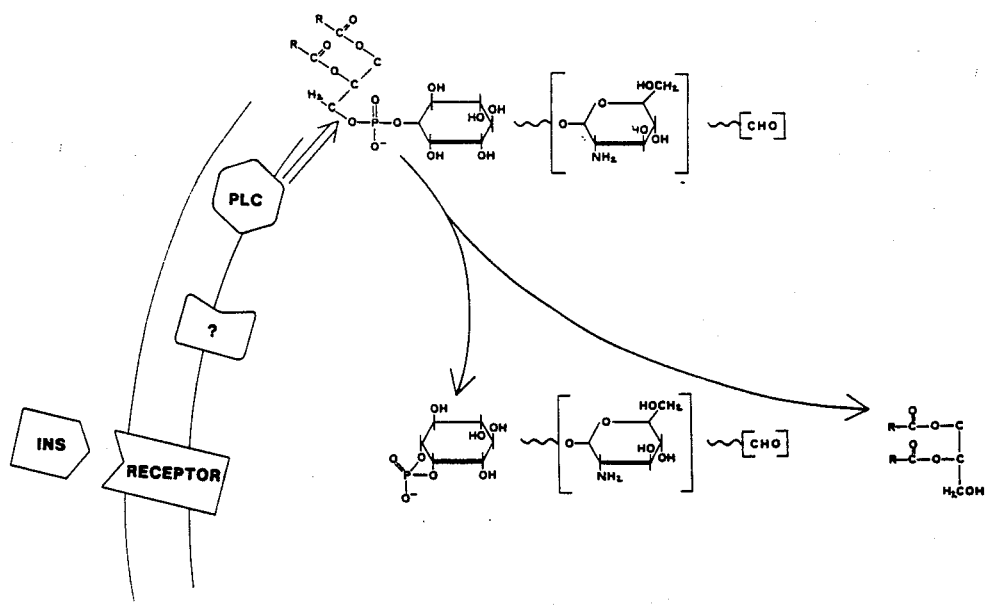

FIG. 15 - Model for Insulin Stimulation of a Phosphoinositide Glycan-Specific Phosphidipase C. Some of the actions of insulin may be mediated by stimulation of the phosphodiesteratic hydrolysis of a novel phosphatidylinositol containing glycolipid. The binding of insulin to its receptor is linked, perhaps through a coupling protein, to the activation of a phospholipase C which selectively hydrolyses a PI-glycan containing glucosamine and other carbohydrates. This hydrolysis results in the generation of two potential signals: 1) an inositor-phosphate glycan messenger activity which regulates cAMP phosphodiesterase and perhaps other insulin sensitive enzymes, and 2) diacylglycerol which may selectively regulate the activity of protein kinase C or an analogous protein kinase.

DETAILED DESCRIPTION

In its primary aspect, the present invention relates to the isolation and identification of particular factors, referred to hereinafter as the insulin activity messenger material and its precursor material, that have been found to be present on the cellular level as a result of the interaction between insulin and its receptors. In particular, the messenger material and the precursor that have been identified and purified to the end extent set forth in accordance with the present invention, present materials that apparently exist on the cellular level and that are enzymatically modified as a result of receptor binding of insulin to act on behalf of insulin to effectuate insulin activity on the cellular level.

In particular, and as will be more fully set forth hereinafter, it has been determined that receptor binding of insulin promotes the phosphodiesteratic cleavage of the precursor material, which results in the formation of the insulin activity messenger material which then exerts its effects upon the cellular system, as exemplified by its effects shown hereinafter on the enzymes pyruvate dehydrogenase, adenylate cyclase, acetyl CoA carboxylase and low Km cAMP phosphodiesterase that is derived from fat or liver cells. The activity of the messenger material with respect to all of these enzymes is reflective of activity directly resulting from the presence and regulatory effect of insulin on the cellular level.

Although the focus of considerable research attention over the past two decades, the molecular mechanisms of insulin action remain largely unexplained. Insulin binds to a heterodimeric cell surface receptor which contains a hormonally responsive tyrosine kinase activity in its $\beta$ subunit. The ensuing changes in cellular metabolism are diverse, occurring within seconds or hours of hormone-receptor interaction. The acute regulation by insulin of enzymes controlling intermediary metabolism is observed within minutes, and is often the result of changes in the phosphorylation state of the enzyme. The precise biochemical link between the activated receptor and enzyme regulation, however, remains unknown.

Several known substances have been proposed to act as second messengers for insulin, yet each has proven inadequate to account for the action of the hormone. More recent reports have suggested that some of the actions of insulin may be accounted for by the generation from the plasma membrane of a unique undefined substance or group of substances which acutely regulate certain insulin sensitive enzymes, perhaps through control of protein phosphorylation. These mediator activities were water soluble, non-nucleotide and exhibited an apparent molecular weight of 1–2000. Although there was suggestion of a peptidic structure, definitive information concerning the chemical identities of these substances has not been forthcoming.

In accordance with the present invention, two such substance, which modulate the activity of the high affinity cAMP phosphodiesterase (PDE), have been purified from hepatic plasma membranes. These two substances have similar properties and activities, but can be resolved by ion exchange chromatograph and high voltage electrophoresis. Both exhibit a net negative charge, even at pH 1.9, and an apparent molecular weight of approximately 1400 daltons. The production of these substance from membranes by insulin can be reproduced by addition of a phosphatidylinositol (PI) specific phospholipase C purified from S. aureus. This enzyme is known to selectively hydrolyze PI and release from membranes several proteins which are covalently linked to PI via a glycan anchor. Both PDE-modulating substances appear to generated from a novel phosphatidylinositol glycolipid precursor which has been identified by thin layer chromatography. Some of the chemical properties of these substances have been examined, indicating a complex carbohydrate-phosphate containing glucosamine and inositol.

Thus, the present invention comprises the identification and preparation of an insulin activity messenger which comprises at least one and possibly two carbohydrate-based compounds that have been found to be capable of modulating the activity of the enzymes pyruvate dehydrogenase, adenylate cyclase, acetyl CoA carboxylase and low Km cAMP phosphodiesterase from fat cells, and thereby effectuating the activity of insulin on the cellular level. The messenger materials may be derived from animal hepatic membranes that have been incubated with a phosphatidyl inositol-specific phospholipase C (hereinafter PI-PLC), as indicated in the above discussion. While the hepatic plasma membranes have shown particular activity in this regard, other tissues have been similarly investigated and found to offer comparable results. Also, the insulin-responsive murine myocyte cell line $BC^3H1$ provides a particularly useful synthetic medium for the in vitro simulation of the activities identified herein, which likewise may serve capably in subsequent assay testing and antibody and drug development activities.

As stated earlier, the insulin activity messenger of the present invention comprises at least one complex carbohydrate having at least one phosphate substituent present as charged group and including a glucosamine component. As will be clear from a review of the examples that follow herein, this data was derived from the purification procedures in Example 1. In particular, the complex carbohydrate may be selected from cyclic 1,2 phosphodiester inositol derivatives and a 1- or a 2-phosphomonoester inositol derivative or mixtures of these, each in comination with a glucosamine component. More particularly and as a result of the analysis of the data generated and set forth herein, it has been determined that the messenger material of the present invention comprises two materials, the first being a mixture of a cyclic 1,2 phosphodiesterinositol derivative and glucosamine, the second being a mixture of either a 1- or a 2-phosphomonoesterinositol derivative, or mixtures of these, also in combination with a glucosamine component.

As mentioned earlier, the present invention also includes a precursor material from which the insulin activity messenger material may be produced by the phosphodiesteratic cleavage catalyzed by PI-PLC. In particular, and as set forth herein, the precursor material has been identified to the extent that it contains diacylglycerol, inositol and glucsoamine components. In other respects, however, this precursor material is chemically undefined.

The present invention also relates to a variety of diagnostic applications, including methods for detecting the onset or presence of insulin sensitivity disorders by measuring the activity of the messenger material or its precursor material. As mentioned earlier, the messenger material can be used to produce antibodies to itself by a variety of known techniques, and such antibodies could then be isolated and utilized as a test for the presence and activity of the messenger material in suspect mammalian hosts.

Antibody(ies) to the messenger material can be produced and isolated by standard methods including the well known hybridoma techniques. The antibody(ies) can be used in another species as though they were antigen(s) to raise antibody(ies). Both types of antibody(ies) can be used to determine the presence and extent of messenger material activity. For convenience, the antibody(ies) to the messenger material will be referred to herein as $Ab_1$ and antibody(ies) raised in another species as $Ab_2$.

Abnormalities in the insulin-sensitive production of messenger material activity in various diabetic disorders can be ascertained by the usual immunological procedures applicable to such determinations. A number of useful procedures are known. Three such procedures which are especially useful utilize either the messenger material labeled with a detectable label, antibody $Ab_1$ labeled with a detectable label, or antibody $Ab_2$ labeled with a detectable label. The procedures may be summarized by the following equations wherein the asterisk indicates that the particle is labeled, and "Mes" stands for the messenger material:

A. $Mes^* + Ab_1 = Mes^*Ab_1$
B. $Mes + Ab_1^* = MesAb_1^*$
C. $Mes + Ab_1 + Ab_2^* = MesAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the messenger material forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using $Ab_1$ as an antigen. $Ab_2$ therefore would be anti-rabbit antibody raised in goats. For purposes of this description and claims, $Ab_1$ will be referred to as a messenger material antibody and $Ab_2$ will be referred to an antibody reactive with a messenger material antibody or, in the alternative, an "anti-antibody".

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The messenger material or its binding partner(s) can also be labeled with a radioactive element or with an enzyme. The radioactive label can be detected by any of the currently available counting procedures. The preferred isotope may be selected from $^{14}C$, $^{131}I$, $^3H$, $^{125}I$ and $^{35}S$.

Enzyme labels are likewise useful, and can be detected by any of the presently utilized colorimetric, spectrophotometric, fluorospectrophotometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and acid phosphatase. U.S. Pat. Nos. 3,654,090; 3,850,752; and 4,016,043 are referred to by way of example for their disclosure of alternate labeling material and methods.

Purified preparations of messenger material added exogenously can regulate the metabolism of intact cells. This suggests the possibility of a receptor-mediated transport system which acts to internalize the substance into the cell.

A particular assay system developed and utilized in accordance with the present invention, is known as a receptor assay. In a receptor assay, the material to be assayed is appropriately labeled and then certain cellular test colonies such as the adipocyte or myocyte cell system are innoculated with a quantity of the labeled material after which binding studies are conducted to determine the extent to which the labeled material binds to the cell receptors. In this way, differences in activity between materials can be ascertained.

In a further embodiment of this invention, commercial test kits suitable for use by a medical specialist may be prepared to determine the presence or absence of messenger material activity in cells or cell extracts derived from patients with obesity or hormonal disorders. In accordance with the testing techniques discussed above, one class of such kits will contain at least the labeled messenger material or its binding partner, an antibody specific thereto. Another will contain at least $Ab_1$ together with labeled $Ab_2$. Still another will contain at least $Ab_1$ and directions, of course, depending upon the method selected, e.g., "competitive", "sandwich", "DASP" and the like. The kits may also contain peripheral reagents such as buffers, stabilizers, etc.

Accordingly, a test kit may be prepared for the detection of the messenger or its precursor, comprising:

(a) a predetermined amount of at least one labeled immunochemically reactive component obtained by the direct or indirect attachment of the present messenger material or a specific binding partner thereto, to a detectable label;

(b) other reagents; and (c) directions for use of said kit.

More specifically, the diagnostic test kit may comprise:

(a) a known amount of the messenger material as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the messenger material to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the messenger material and a specific binding partner thereto.

In accordance with the above, an assay system for screening potential drugs effective to mimic, counteract or potentiate the messenger material, or to enhance or block its production, may be prepared. In a first procedure, the test drug could be administered to a hormonally sensitive cell to determine its effect upon cellular metabolism. In an alternate procedure, the messenger material may be introduced into a cellular test system such as the adipocyte or myocyte BC3Hl and the prospective drug may then be introduced into the resulting cell culture, and the culture thereafter examined to observe any changes in the activity of the messenger material, either from the addition of the prospective drug alone, or the effect of added quantities of the known messenger material. Moreover, the ability of a test drug to prevent or stimulate the production of the messenger activity could be screened.

As indicated earlier, the following examples set forth the details of the isolation and identification of the present messenger material, and the observations noted as to its activity, defining both the distinctions and similarities in activity between the present messenger material and those factors identified earlier both by applicants and by others in the field. Naturally, the specific materials and techniques set forth hereinafter are exemplary only and may vary, so that the following is presented as illustrative but not restrictive of the present invention.

EXAMPLE I

EXPERIMENTAL PROCEDURES

Materials

All reagents were from Sigma, with the exception of collagenase (Millipore), DEAE-Cellulose and SAX HPLC columns (Whatman), C-18 reverse phase resin (Waters), P-2 gel filtration media, P-2 gel filtration media, Dowex AG-1X8 and Dowex 50WX-4 (BioRad), QAE Sephadex (Pharmacia) and 2,8[$^3$H]cAMP (NEN). Male rats (100–125 g) were from Sprague-Dawley. Monocomponent bovine insulin was from Wellcome Laboratores, Beckenham, UK. Purified phosphatidylinositol specific phospholipase C (PI-PLC) from S. aureus was a generous gift from Dr. M. Low of the Oklahoma Medical Research Foundation.

Generation of cAMP Phosphodiesterase Modulators by Insulin

These were generated from bovine liver particulate fractions by a modification of previously described methods. Particulate fraction was prepared from 100 g of bovine liver, and suspended in 500 ml mM ammonium bicarbonate, pH 7.4. (Buffer A) at a final concentration of 2–4 mg protein/ml. This solution was incubated with 10 mM for 10 min at 37° C., acidified to pH 4.0 with formic acid and sedimented at 45,000 g for 20 min. An equal volume of chloroform/methanol (2:1) was added to the supernatant, and the upper phase was aspirated and methanol was evaporated.

Extraction of the Glycolipid Precursor

Particulate fraction was suspended in buffer A as described above and lyophilyzed. The resulting powder was extracted in 500 ml of chloroform/methanol/IN HCl (200:100:1) by agitation for 30 min followed by filtration. The filtrate was evaporated to near dryness and resuspended in buffer A or purified further on silica TLC. Oxalate pretreated silica gel G plates were preactivated at 60° for 1 hr., and twice developed in chloroform/acetone/methanol/glacial acetic acid/H$_2$O (10:4:2:2:1). One cm regions were scraped, and lipids eluted with methanol. Samples were dried and resuspended in buffer A by sonication.

Hydrolysis of the Glycolipid Precursor by PI-PLC

Extracted lipids were treated with 1.0 g/ml S. aureus PI-PLC for 30 min at 37° C. in buffer A. Following incubation, samples were acidified to pH 4.0 and PDE-messengers were extracted with chloroform/methanol as described above.

Assay of cAMP Phosphodiesterase Activity

The low Km cAMP phosphodiesterase (PDE) from rat adipocyte particulate fraction was assayed. Rat fat cells were fractionated on discontinuous sucrose density gradients as previously described. cAMP PDE was measured for 10 min at 30° C. by the method of Thompson and Appleman as modified previously. Only the high affinity enzyme was present in this subcellular fraction. Activity was proportional to protein concentration and linear throughout 30 min. Results are means of triplicate determinations in which variability was less than 5%. Protein concentration was measured by the method of Lowry et al.

High Voltage Thin Layer Electrophoresis

Purified mediator fractions were subject to high voltage electrophoresis on cellulose coated thin layer plates. Plates were subject to 500 volts for 1 hr. at pH 3.5 or 1.9. 1 cm regions were scraped, eluted with 50% methanol in 10 mM formic acid, lyophilized and assayed for PDE modulating activity following resuspension in 10 mM formic acid.

RESULTS

Purification of the Messengers

The protocol for this procedure is outlined in Table I, below.

TABLE I

Purification of PDE-messengers

1. Extraction of supernatant with chloroform/methanol
2. DE-52 anion exchange
3. C-18 reversed phase
4. Dowex 50 W X 8 cation exchage
5. Charcoal adsorption
6. QAE-Sephadex anion exchange
7. aSAX HPLC anion exchange
8. P-2 gel filtration Following extraction from the supernatants of liver membranes, PDE modulating activity was chromatographed on a 40 ml column of DEAE-Cellulose (DE-52), washed with 2 column volumes of 0.05M ammonium formate, pH 4.0 and eluted with 2 column volumes of 0.25M TEA-formate, pH 3.75. This fraction was chromatographed on 30 ml of C-18 reversed phase resin, loaded and eluted in 0.25M TEA-formate, pH 3.75.

Figure 1:
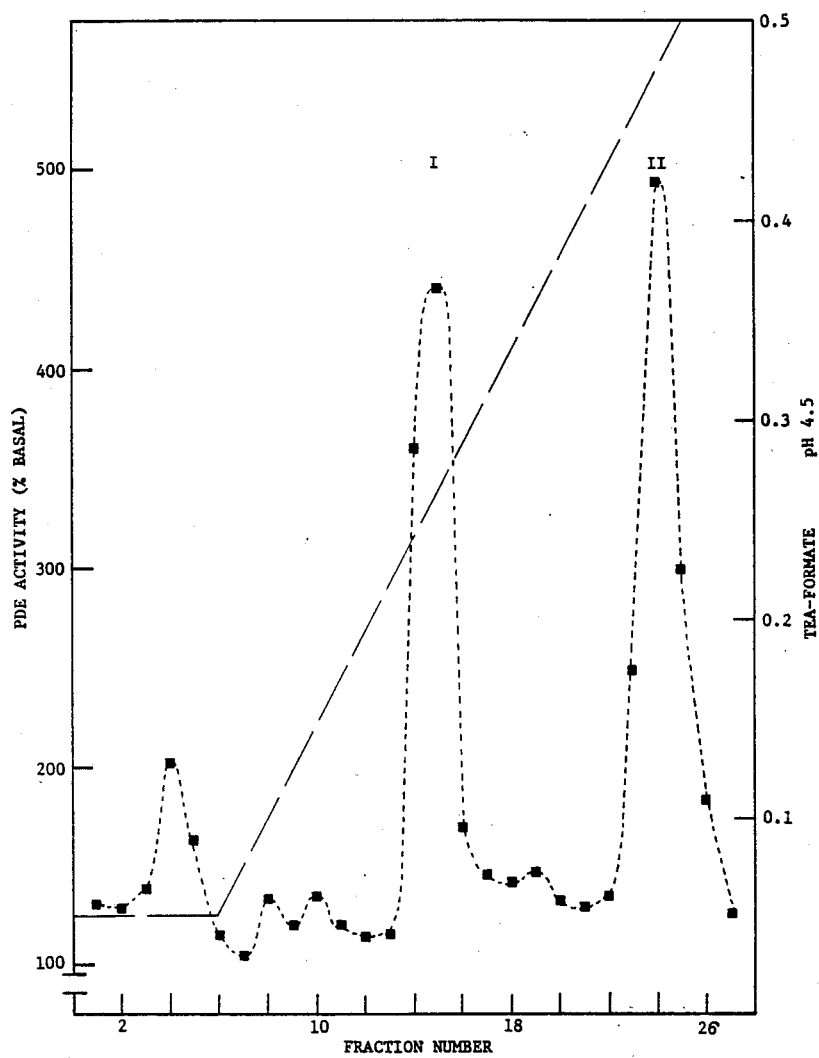
FIG. 1 - QAE-Sephadex Chromatography of PDE-Modulating Activities. Partially purified extracts from liver membranes were loaded onto a 10 ml QAE-Sephadex column, equilibrated in 0.05 M TEA-formate, pH 4.75. The column was eluted with a 40 ml linear gradient of 0.05–0.50 M TEA-formate, pH 4.75 as shown: 2 ml fractions were lyophilized, resuspended in 0.5 ml 10 mM formic acid and assayed at a 1:10 dilution for ability to stimulate cAMP phosphodiesterase in adipocyte plasma membranes.

PDE modulating activity was not retained on this column. Following lyophilization, sample was resuspended in 20 ml of 0.05M TEA-formate, pH 3.0, and chromatographed on a 20 ml Dowex 50W X-4 cation exchange column, eluted in the same buffer. Under these conditions, activity was not retained on this column. The elute was lyophilized, resuspended in 0.05M TEA-formate, pH 4.5 and treated with activated charcoal for 10 min at 4° C. The nonadsorbed supernatant was then chromatographed on a 10 ml QAE-Sephadex column, eluted with a linear gradient of 0.05M TEA-formate, pH 4.75 (FIG. 1). One ml fractions were lyophilized, resuspended in 10 mM formic acid and assayed for PDE modulating activity.

Figure 2:
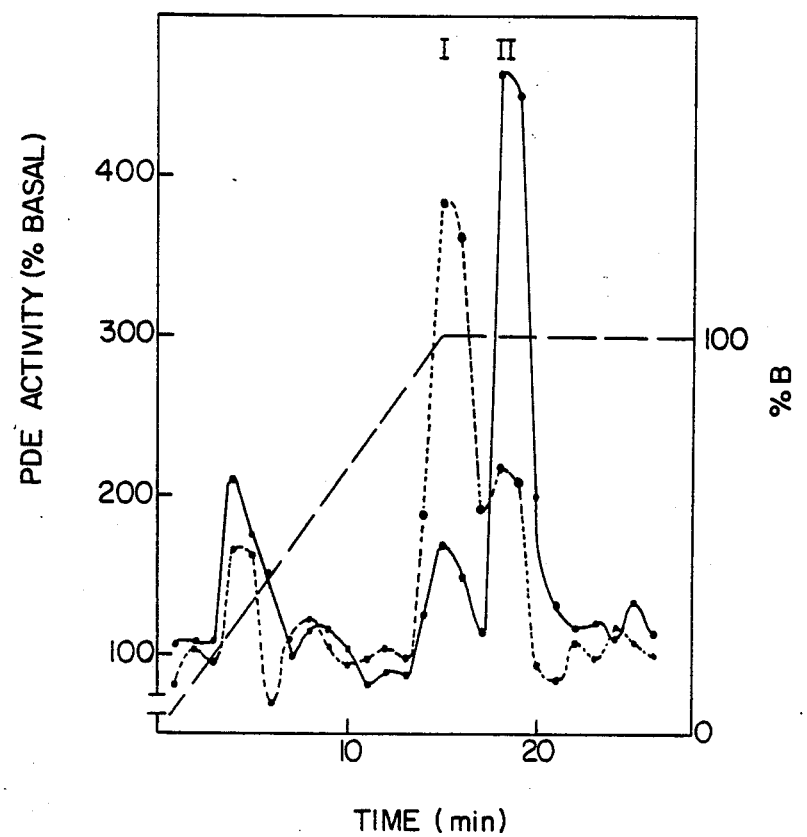
FIG. 2 - Analytical SAX HPLC of PDE-Modulating Activities. Peaks I and II from QAE-Sephadex were separately pooled and injected onto an analytical SAX HPLC column, equilibrated with 60% methanol and eluted at 1 ml/min with a linear, 15 min gradient to 0.5 M TEA-formate, pH 3.75. One ml fractions were lyophilized, resuspended in 0.5 ml 10 mM formic acid and assayed for PDE-modulating activity.
Figure 3:
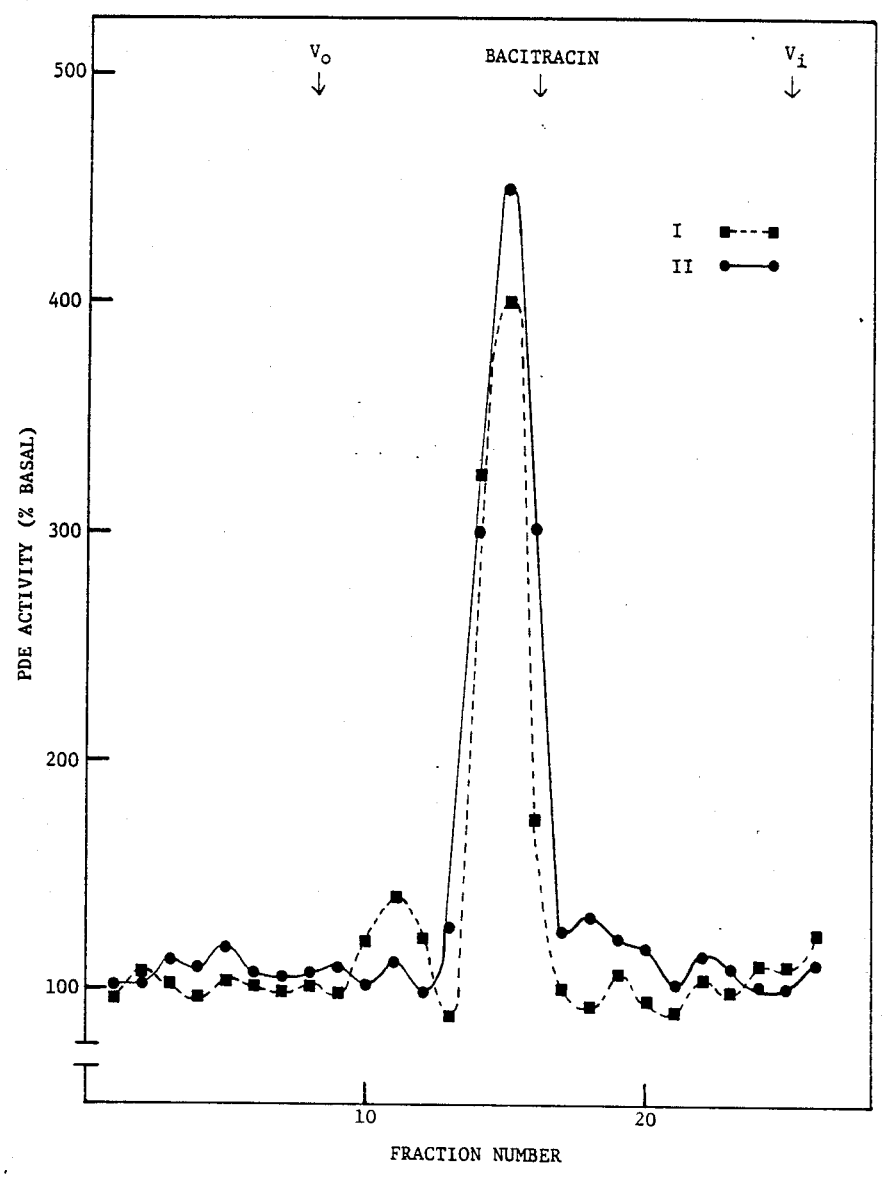
FIG. 3 - P-2 Gel Filtration of PDE-Modulating Activities. Pooled active fractions from analytical SAX were loaded onto a 25 ml P-2 column and eluted with 50 mM formic acid. One ml fractions were lyophilized, resuspended in 0.5 ml 10 mM formic acid and assayed for PDE-modulating activity.

Two species of activity were detected, eluting at approximately 0.25 (I) and 0.45M (II) TEA-formate. Each peak was then chromatographed on an analytical SAX HPLC column (FIG. 2). One ml fractions were lyophilized and assayed. Peaks I and II eluted as distinct components of activity at 15 and 18 min respectively. The active fractions were then separately chromatographed on a 25 ml P-2 gel filtration column (FIG. 3). Under these conditions both peaks eluted with the same approximate volume as did bacitracin (MW=1400).

Figure 4:
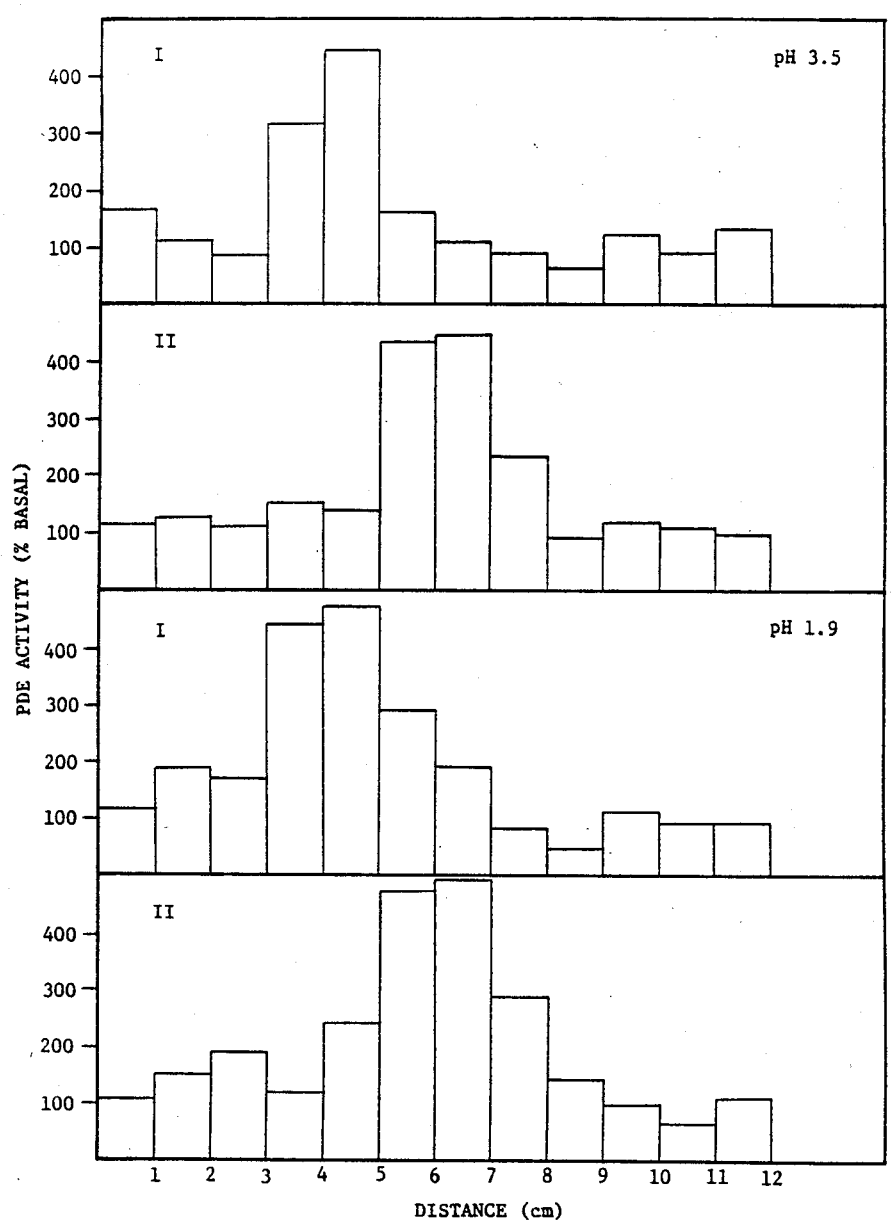
FIG. 4 - High Voltage Thin Layer Electrophoresis. Purified PDE modulators were spotted on cellulose thin layer plates and eletrophoresed at 500 volts for 1 hr. at pH 3.5 (pyridine/glacial acetic acid/$H_2O$ (1:10:189)) or pH 1.9 (88% formic acid/glacial acetic acid/$H_2O$ (50:56:1794)). One cm regions were scraped, eluted with 50% methanol in 10 mM formic acid, evaporated to dryness, resuspended in 0.05 ml 10 mM formic acid and assayed. Inositol monophosphate migrated towards the top of the plate.

PDE Modulating activities were further characterized by high voltage thin layer electrophoresis (FIG. 4). Both substances were electrophoresed at pH 3.5 and 1.9, eluted from plates and assayed. Each species of activity migrated towards the anode although Peak II migrated slightly farther than Peak I at pH 3.5. At pH 1.9, Peak I migrated in a broader region, indicating the possible conversion of some fraction of this activity.

Messengers are Produced by Incubation of Membranes with PI-PLC

In crude extracts of plasma membrane derived supernatants, production of pyruvate dehydrogenase modulating activity was enhanced by insulin. These results were confirmed for production of PDE modulating activities Table II, below.

TABLE II

Effect of Insulin and Phospholipase C on Generation of PDE Messenger from Liver Membranes

| Membrane Treatment | PDE Activity pmol mg protein$^{-1}$ min$^{-1}$ | (% Basal) |
|---|---|---|
| none | 78.5 | (141) |
| 1.0 nM Insulin | 138.0 | (246) |
| 1.0 μg/ml PI-PLC | 191.3 | (341) |
| Insulin + PI-PLC | 197.5 | (352) |

In the tests the results of which are tabulated above, liver membranes were treated as indicated for 10 min at 37° C., centrifuged and supernatants were extracted and purified up to and including the Dowex 50WX-4 step as described earlier herein under "Experimental Procedures". Partially purified extracts were assayed for ability to modulate cAMP phosphodiesterase. Basal activity was 56.2 pmoles/mg protein$^{-1}$−min$^{-1}$.

Insulin treatment of plasma membranes resulted in a 4-fold stimulation of PDE modulating activity detected after partial purification. To probe the mechanism by which this process occurs, purified PI-PLC from S. aureus was added to membranes at a final concentration of 1.0 μg/ml. This enzyme is known to hydrolyze PI and release proteins which are covalently linked to phospholipids via an inositol containing glycan anchor. The enzyme is free of protease activity and does not hydrolyze polyphosphoinositides or other phospholipids.

PI-PLC addition caused a 6-fold increase in the production of messengers from membranes (Table II). Moreover, pretreatment of membranes with PI-PLC for 30 min at 37° C., followed by washing, prevented the further release of activity by insulin (data not shown), suggesting that prolonged exposure of plasma membranes to exogenously added PLC depleted the substrate for the action of insulin. Further purification of the messengers produced by PI-PLC revealed two peaks of activity with chromatographic and electrophoretic properties identical to those produced by insulin (data not shown).

Identification of a Precursor for the Messengers

Figure 5:
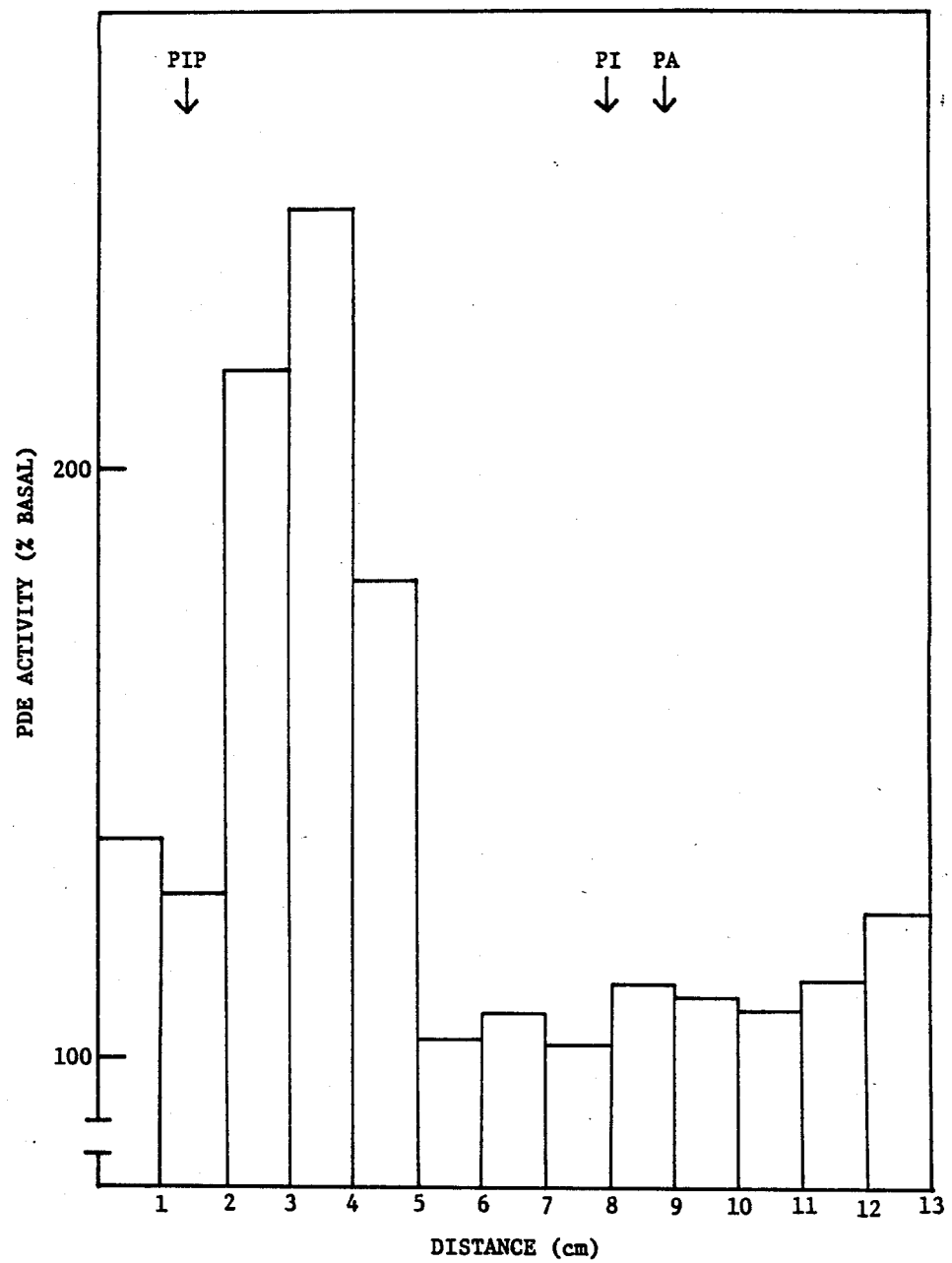
FIG. 5 - Thin Layer Chromatography of Precursor Glycolipid. Organic extracts of liver membranes were streaked onto an oxalate impregnated silica gel G plate, which was twice developed in chloroform/acetone/methanol/glacial acetic acid/$H_2O$ (10:4:2:21). One cm regions were scraped and eluted with methanol. Lipids were dried under $N_2$, resuspended in 1 ml 50 mM ammonium bicarbonate, pH 7.4 and treated with PI-PLC for 30 min. PDE-modulators were extracted as detailed in Example I and assayed.

It was attempted to identify the membrane associated substrate for PI-PLC, which serves as a precursor for generation of the messengers. Organic extracts of hepatic membranes were chromatographed on TLC as described in "Experimental Procedures" and lipids were eluted, treated with PI-PLC and extracted (FIG. 5). A single spot of precursor activity was detected on TLC (Rf=0.28), which migrated faster than phosphatidylinositol-4'phosphate, but slower than PI. Further purification of the PI-PLC generated activity revealed two PDE modulating substances with chromatographic properties identical to those produced from membranes by insulin (data not shown).

Dose Dependence of Messenger Action

Figure 6:
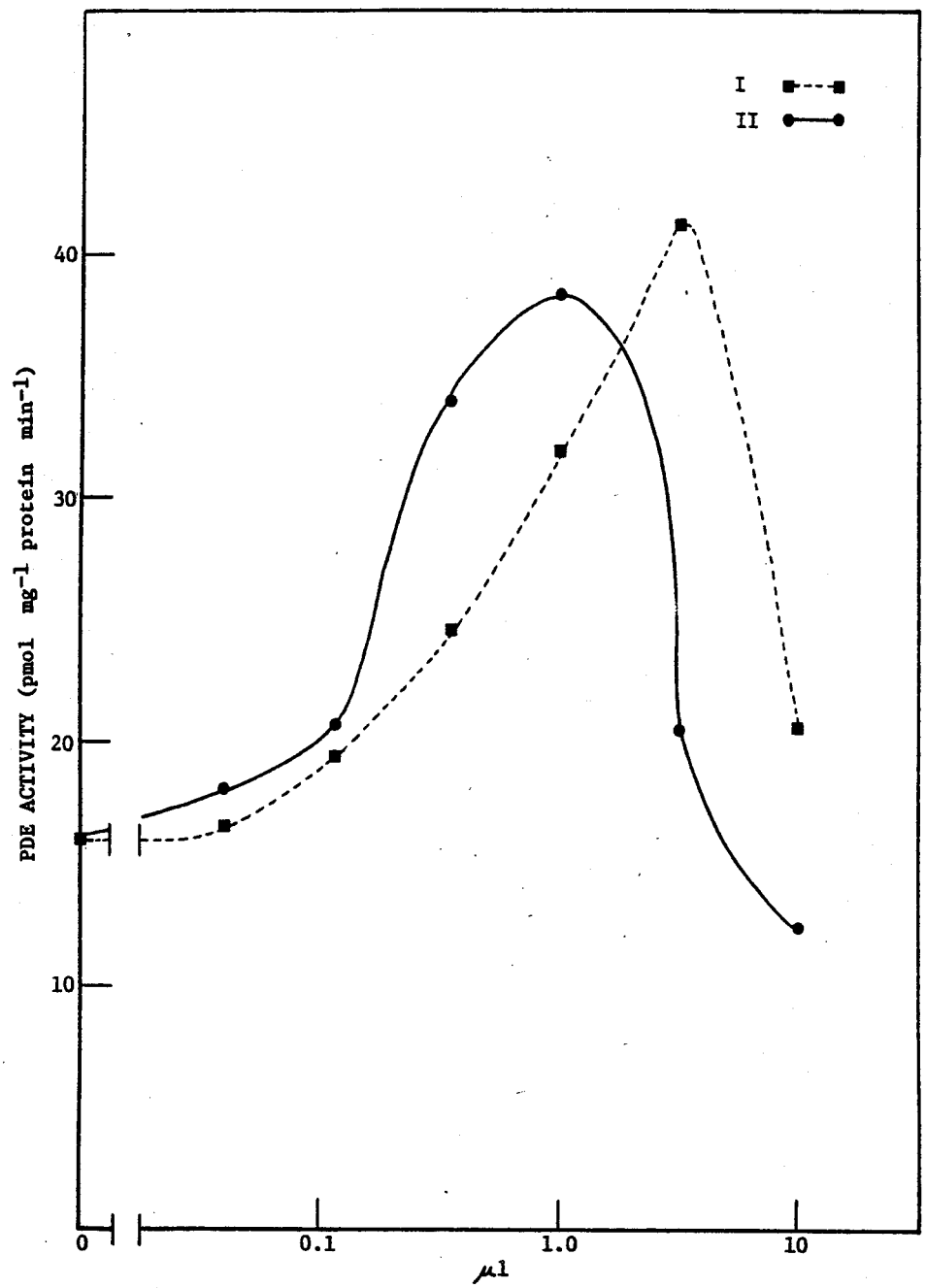
FIG. 6 - Dose Dependence of PDE Modulation. The activity of cAMP phosphodiesterase was evaluated as a function of concentration of modulator. Purified Peak I or II was added to adipocyte particulate fraction of designated dilution and PDE activity was assayed.

The dose dependence of action of Peaks I and II were evaluated (FIG. 6). The response of cAMP PDE to both substances was biphasic with respect to concentration, suggesting that the previously described separation of antagonistic regulators may have reflected resolution of two distinct compounds, each of which similarly exhibited paradoxical dose responses yet were present in dissimilar concentrations or with dissimilar potencies.

Chemical Properties of the Messengers

Several chemical properties of the biological activities residing in Peaks I and II were evaluated, as summarized in Table III, below.

TABLE III

Chemical Modification of the Messengers

| Treatment | PDE Stimulation (% Control) |
|---|---|
| none | 100 |
| 0.1% TFA, 3 hrs. | 100 |
| 10% TFA, 3 hrs. | 10 |
| 0.1% NH$_4$OH, 3 hrs. | 21 |
| 10% HN$_4$OH, 3 hrs. | 0 |
| Diazomethane, 1 hr. | 0 |
| Methanolic HCl, 1 hr. | 0 |
| Na Periodate: .01M, 2 hrs., pH 6.0 | 100 |
| Na Periodate: 1.1M, 24 hrs., pH 6.0 | 27 |
| Na Nitrite: 0.2M, 3 hrs., pH 3.75 | 29 |

With regard to the above data, purified PDE Modulating activity residing in Peak I was subject to indicated treatments at room temperature, and assayed for ability to stimulate PDE. Results are expressed as % stimulation of activity with untreated mediator. For diazomethane treatment, control activity was measured after exposure to diethyl ether for 1 hr, which had no effect on activity. For methanolic HCl treatment, control activity was measured in 100% methanol, which did not effect activity. Periodate and nitrite treatments were compared to treatments in buffer alone, which did not effect activity. Identical results were obtained for activity residing in Peak II.

Activities of both substances exhibited similar susceptibility to strong acid and base. Each was inactivated by methylation with diazomethane or methanolic HCl. Each was partially susceptible to periodate oxidation, perhaps suggesting a carbohydrate structure without readily oxidizable hydroxyl groups. Deamination of glycosidically linked glucosamine with nitrous acid at pH 3.75 simultaneously converts the residue to the 2,5 anhydromannose derivative with hydrolysis of the glycosidic linkage. PDE modulating activities residing in both peaks were 80% inactivated by nitrous acid deamination at pH 3.75.

DISCUSSION

The above experiment details the purification of two substances from hepatic membranes which modulate the activity of the low Km cAMP phosphodiesterase in fat cells. These substances similarly regulate pyruvate dehydrogenase, adenylate cyclase and acetyl CoA carboxylase (unpublished observations). They are rapidly produced in response to physiological levels of insulin, suggesting a role as mediators of some of the action of the hormone.

Several properties of these mediator substances have been studied. The acid stability, alkaline lability and non-nucleotide nature of these activities have been previously suggested, as well as a molecular weight of 1000–2000 daltons. Although a peptide structure has been suggested the activities of the purified substances described here were unaffected by proteolytic enzymes. Moreover, neither substance reacted with ninhydrin (data not shown). Behavior or ion exchange columns and migration on high voltage electrophoresis suggest that the two components contain dissimilar net negative charges, even at pH 1.9. This indicates the presence of phosphate or sulfate as a charged functional group. Both substances appear relatively polar, based upon water solubility and inability to absorb to reversed phase resin. Limited oxidation by periodate indicated the presence of carbohydrate in the active substance. This was further supported by loss of activity after nitrous acid deamination, which implied glycosidically linked glucosamine in the active compound. The presence of an inositol phosphate derivative was strongly suggested by the generation of the activities by a PI specific PLC. Preliminary carbohydrate analysis of the purified fractions after methenolysis revealed inositol phosphate, glucosamine and other monosaccharides.

As has been described, two species of messenger activity can be detected. Although previously suggested to produce antagonistic regulation of insulin target enzymes, it is now believed that these substances share similar bimodal activities with respect to dose dependence. Dissimilar concentrations of substance which both produce paradoxical dose responses, perhaps with different potencies, may explain the apparent resolution of stimulatory and inhibitory activities. Biphasic responses of target enzymes to these substances may account for the paradoxical effects of insulin on lipolysis, adenylate cyclase, and cAMP PDE. Aside from apparent differences in charge and solubility, no difference in the size or chemical sensitivities of these two substances were detected. Since they are both generated by PI-PLC hydrolysis of intact membranes or of an isolated putative glycolipid precursor, one possibility is that they may represent a 1,2-cyclic phosphate and 1- or 2-monophosphate inositol derivative, as has been described for the phosphodiesteratic cleavage of the phosphoinositides and the PI anchored variant surface glycoprotein from *trypanosoma brucei*.

Of considerable interest was the finding that the substrate for the PI-PLC catalyzed generation of the mediators could be identified by the organic extraction of liver membranes. The identification of this putative precursor as an inositol and glucosamine containing glycolipid has been verified in primary cultures of hepatocytes and cultured myocytes by preincubation of cells with [$^3$H]inositol and [$^3$H]glucosamine. In these experiments which follow below, radioactivity from both sources was incorporated into a glycolipid with a Rf on TLC identical to the precursor described here. The radioactivity in this precursor was rapidly diminished by insulin in intact cells and by treatment of extracted lipids with exogenous PI-PLC. [$^3$H]inositol and [$^3$H]glucosamine were rapidly incorporated into fractions containing purified messenger in response to both insulin (cells) and PI-PLC (extracted lipids).

EXAMPLE II

The studies on enzymatic production of the activities of the messenger materials purified and characterized in Example I with a PI specific PLC, and evaluation of chemical sensitivities suggested that the enzyme modulating activity of these messengers was derived from substances which contained inositol and glycosidically linked glucosamine. In the present example, the actions of insulin of the production of the mediator substances were evaluated in the cultured murine myocyte line BC$_3$H1. These cells become responsive to insulin upon differentiation following attainment of confluence. The insulin sensitive incorporation of radioactive inositol and glucosamine into HPLC fractions which contain activities ascribed to the messengers was observed. The production of these radioactive products mirrors that of the enzyme modulating activities, and appears to be due to the hydrolysis of a novel glycolipid precursor.

Radioisotopic Labeling of the Messengers

The purification procedure of Example I was modified for purification of similar substances from BC$_3$H1 cells incubated with [$^3$H]inositol or [$^3$H]glucosamine. Following insulin treatment and extraction, the aqueous phase was sequentially chromatographed on DEAE-Cellulose, C-18 reversed phase and Dowex 50WX-4 cation exchange. This was followed by chromatography on an SAX HPLC column (FIG. 7). Insulin treatment increased the incorporation of [$^3$H]inositol into two peaks which eluted at 15 (I) and 18 (II) min. Minimal incorporation into these fractions was observed in control cells (FIG. 7a). Insulin had a similar effect on incorporation of [$^3$H]glucosamine into identical fractions (FIG. 7b), although another radioactive peak was detected at 23 min. which was unaffected by insulin. These two peaks of insulin stimulated radioactivity exhibited distinct retention times from those of 1,2 cyclic inositol monophosphate (10 min.) or inositol monophosphate (24 min.). However, Peaks I and II coeluted with two peaks of PDE modulating activity produced in these cells in response to insulin. These myocyte derived activities were indistinguishable from those purified from insulin treated liver plasma membranes.

PDE messengers can be produced from liver membranes by addition of PI-PLC from S. aureus. These enzyme specifically hydrolyzes the phosphodiester linkage of phosphatidylinositol and those proteins covalently attached to PI via a glycan anchor. These preparations of PI-PLC were free of protease activity, and were inactive against polyphosphoinositides and other phospholipids. Cells were preincubated with [$^3$H]inositol or [$^3$H]glucosamine, and lipids were extracted and treated with PI-PLC. After a 30 min. incubation, cells were extracted, the aqueous products were purified as described above and chromatographed on an SAX HPLC column (FIG. 8). PI-PLC treatment resulted in the generation of two peaks containing [$^3$H]inositol which exhibited retention times identical to those produced by insulin in intact cells. [$^3$H]glucosamine was also incorporated into these fractions in response to PI-PLC, although a spontaneously released peak was observed at 23 min. which was unaffected by PI-PLC.

Identification of Putative Radiolabeled Precursor

Described above is a chemically unidentified glycolipid in liver plasma membranes which appeared to serve as a substrate for the generation of PDE messengers by the S. aureus PI-PLC. The incorporation of [$^3$H]inositol and [$^3$H]glucosamine into these putative precursor was examined in BC$_3$Hl cells. Thin layer chromatography of extracted phospholipids revealed a peak into which both [$^3$H]inositol and [$^3$H]glucosamine were incorporated (FIG. 9). This glycolipid exhibited an Rf identical to the putative precursor of the PDE messenger from liver. It migrated faster than phosphatidylinositol 4 phosphate but slower than phosphatidylinositol. After treatment of cells with insulin for 10 min., the incorporation of both [$^3$H]inositol (FIG. 9a) and [$^3$H]glucosamine (FIG. 9b) in this peak was increased approximately 40%, with no significant change in labeling of other lipids. In parallel experiments, lipids were extracted from labeled cells and treated with or without PI-PLC for 30 min. (FIG. 10). Exposure to this enzyme caused a 60% decreased in [$^3$H]inositol labeling (FIG. 10a) and 40% decrease in [$^3$H]glucosamine labeling (FIG. 10b) of an identical spot on PLC. As expected, PI was 50% depleted by the S. aureus PI-PLC. Similar result, have been observed by PI-PLC treatment of plasma membranes prepared from these labeled myocytes.

Time Course of the Phosphodiesteratic Cleavage of the Glycolipid Precursor

The time course of radioisotipic incorporation into the products and putative precursor described above was examined after exposure to cells to 10 nM insulin (FIG. 11). In these experiments, the water soluble products were sequentially chromatographed as described above, and results represent a combination of Peaks I and II from HPLC. Insulin rapidly stimulated the production of these [$^3$H]inositol containing products. Seventy percent of the maximal effect was achieved after 30 sec. The time course of [$^3$H]inositol incorporation into the precursor (as identified on TLC in FIGS. 9 and 10) was biphasic. Insulin caused a small (20%) but significant decrease in counts at 30 sec. Thereafter, radioactivity in this peak increased, resulting in a 60% increase over control levels.

The phosphodiesteratic cleavage of a phospholipid by insulin should also be reflected by increased production of diacylglycerol, which could serve as substrate for a diglyceride kinase, producing phosphatidic acid. Myocytes were preincubated with [$^3$H]myristic acid and both diacylglycerol and phosphatidic acid labeling were evaluated by thin layer chromatography (FIG. 6). Insulin caused a 40% increase in [$^3$H]myristate diacylglycerol within 1 minute. Labeled diacylglycerol decline to near basal levels by 2 minutes, and then increased, reaching a maximal 50% increase over basal by 5–10 minutes. Labeled diacylglycerol production was followed by a 2 fold increase in levels of [$^3$H]myristate phosphatidic acid, achieved by 5 minutes. [$^3$H]myristate diacylglycerol was also rapidly produced by incubation of extracted lipids with S. aureus PI-PLC (data not shown).

Further Characterization of the Water Soluble Radiolabeled Products

The chromatographic properties of the [$^3$H]inositol and [$^3$H]glucosamine labeled products from insulin treated BC$_3$Hl cells were further evaluated. Pooled radioactivity residing in SAX Peak I was chromatographed on a P-2 gel filtration column (FIG. 13). The elution profiles of [$^3$H]inositol (FIG. 13a) and [$^3$H]glucosamine (FIG. 13b) labeled products were compared with that of the similarly purified myocyte derived PDE modulating activity (FIG. 7c). Each substance eluted in an identical volume indicating an approximate molecular weight of 1400. Both radioactive and bioactive substances in Peak II exhibited an identical elution on P-2 (data not shown). Following P-2 gel filtration, active samples were pooled and subject to high voltage electrophoresis on cellulose coated thin layer plates (FIG. 14). The electrophoretic migration of both labeled products in Peak I was identical to that of the PDE messenger. Similar results were obtained when samples were electrophoresed at pH 1.9. Radioactively labeled products and PDE messenger activity residing in Peaks II migrated slightly farther than that of Peak I at both pHs (not shown) as described previously, although comigration of radioactivity and bioactivity was again observed. These results confirm previous findings of dissimilar net negative charge for these compounds, implicating phosphate or sulfate as charged species.

To further evaluate differences in the two products each of the [$^3$H]inositol labeled peaks was digested at 25° C. for 16 hrs. with alkaline phosphatase (100 U/ml) in 50 mM ammonium bicarbonate, pH 8.0. Each sample was then injected onto a SAX column, and counts in each peak were determined. Alkaline phosphatase treatment had no effect on counts of Peak I, but produced a 70% loss of counts in Peak II as shown in Table IV, below.

TABLE IV

Modification of [$^3$H]Inositol Labeled Products

| Treatment | dpm Peak I | dpm Peak II |
|---|---|---|
| none | 1820 | 1100 |
| Alkaline Phosphatase (10 μg/ml) | 1963 | 341 |
| Nitrous Acid (0.2 M, pH 3.75) | 220 | 195 |

Following gel filtration, purified [$^3$H]inositol labeled products in Peaks I and II were treated with (a) alkaline phosphatase (10 U/ml) in 50 mM ammonium bicarbonate, pH 8.0 for 16 hrs. at 30° C., or (b) 0.2M Na Nitrite in 50 mM ammonium acetate, pH 3.75 for 3 hrs. at 25° C. Following incubation, samples were injected into SAX HPLC column, eluted as detailed in FIG. 7, and collected in buffer alone, all counts were recovered with the appropriate retention time.

These results were consistent with the possibility that Peak I contains a cyclic 1,2 phosphodiester inositol derivative which is not susceptible to alkaline phosphatase, whereas Peak II may contain phosphomonoester inositol derivative which is hydrolyzed by alkaline phosphatase.

Treatment with nitrous acid at pH 3.75 deaminates glycosidically linked glucosamine, converting the residue to a 2,5 anhydromannose derivation involving cleavage of the glycosidic linkage. Treatment of purified [$^3$H]inositol labeled products in both peaks with nitrous acid caused an 80% loss of counts detected after HPLC (Table IV). These results were verified by measurement of radioactivity on high voltage electrophoresis. Eighty-five percent of [$^3$H]inositol migrated as inositol monophosphate after nitrous acid deamination (data not shown).

DISCUSSION

Upon differentiation, the cultured myocyte line, BC$_3$Hl, develops affinity insulin receptors and several biological responses to the hormone, including glucose transport, amino acid uptake, insulin receptor down-regulation and increased labeling of certain phospholipids. The above experiments confirm that the apparent phosphodiesteratic cleavage of a chemically unidentified glycolipid resulting in the generation of two water soluble products as well as diacylglycerol. Both the products and putative precursor of the reaction have been identified by radioisotopic labeling with [$^3$H]inositol and [$^3$H]glucosamine. These labeled compounds appear to be incorporated into the water soluble products with a 1:1 stoichiometry. The insulin dependent hydrolysis of the putative glycolipid precursor, and subsequent appearance of the products occurs in less than 1 min. Thereafter, [$^3$H]inositol incorporation into the precursor increases, suggesting its rapid resynthesis. This process appears similar to that observed in the hormone stimulated phosphodiesteratic cleavage of the phosphoinositides, in which these phospholipids are rapidly replenished.

The hydrolysis of the putative precursor described here and subsequent generation of carbohydrate products and diacylglycerol were also accomplished by treatment of extracted phospholipids with S. aureus PI-PLC, which specifically hydrolyzes phosphatidylinositol and releases proteins covalently anchored to phosphatidylinositol. Thus, insulin action may involve activation of an endogenous PLC activity which hydrolyzes a novel inositol/glucosamine containing glycolipid. Since insulin does not stimulate hydrolysis of polyphoshoinositides, the insulin sensitive PLC may be similar to the PLC activity identified in *trypanosoma brucei* which selectively attacks the glucosamine/inositol phosphodiester anchor of the membrane bound variant surface such a selective PLC in insulin action is supported by observations that the purified trypanasoma PLC is an effective as the S. aureus enzyme in hydrolysis of the myocyte glycolipid precursor.

The water soluble products of the putative phosphodiesteratic hydrolysis stimulated by insulin have been purified and characterized. Coincorporation of [$^3$H]inositol and [$^3$H]glucosamine was observed into identical fractions on distinct chromatographic and electrophoretic systems. Characterization of net charge (ion exchange), size (gel permeation), mass charge ratio (high voltage electrophoresis) and hydrophobicity (reversed phase) indicated that labeled inositol and glucosamine are incorporated into the same products in an insulin dependent manner. Although it is possible that these labeled precursors were first converted to other sugars during preincubation, the incorporation of intact myo-inositol was supported by the selective hydroloysis of the putative precursor and generation of product by PI-specific phospholipase C. Moreover, glucosamine incorporation was validated by loss of radioactivity in purified fractions after nitrous acid deamination under conditions specific for cleavage of glycosidically linked glucosamine.

The insulin sensitive products labeled with [$^3$H]sugars cochromatographed with insulin stimulated messengers, derived both from BC$_3$Hl myocytes and liver plasma membranes. Bioactivity and radioactivity from those sources exhibited identical electrophoretic and chromatographic behavior on each system and under all conditions. PDE modulating activities were produced by insulin over the same time course and concentration range as were the purified radiolabeled products (data not shown). Identical species of bioactivity and labeled products were generated by treatment of membranes or extracted phospholipids with S. aureus PI-PLC. These results indicated that the activities of the insulin generated PDE messengers can be ascribed to the radiolabeled complex carbohydrates described here.

The two insulin sensitive, radiolabeled products from myocytes resolved by ion exchange chromatography to correlate with the two species of PDE modulating activity derived from liver. These two peaks share several chemical properties, yet exhibit dissimilar net negative charges, even at pH 1.9. Since both substances were generated by PI-PLC hyrolysis of a membrane glycolipid, one possibility is that they represent a 1,2-cyclic monophosphate (Peak I) and 1- or 2-monophosphate (Peak II) inositol derivatives. Such cyclic products have been identified for the phosphodiesteratic cleavage of phosphoinositides and the PI anchored variant surface glycoprotein from *trypanosoma brucei*. This hypothesis is supported by the susceptibility of [$^3$H]inositol labeled Peak I was unaffected by the enzyme.

The chemical identity of the putative glycolipid which serves as substrate for insulin stimulated hydrolysis remains undefined. This novel glycolipid shares some characteristics with the membrane glycan anchor described from the trypansoma variant surface glycoprotein, which consists of phosphate, glucosamine and myo-inositol as well as ethanolamine and other carbohydrates. It appears that insulin causes the phosphodiesteratic cleavage of such a phospholipid, resulting in the generation of two closely related carbohydrate products which may mediate some of the acute actions of insulin. Included in this process is the obligatory production of diacylglycerol, the endogenous activator of protein kinase C. Although in previous reports, diacylglycerol production by insulin was previously attributed to stimulation of de novo synthesis, the transient generation of diacylglycerol has been observed in response to insulin, followed by the apparent rapid phosphorylation to phosphatidic acid. Diacylglycerol and the [$^3$H]inositol labeled products appeared to arise from the same precursor, and their production was kinetically indistinguishable. It is possible that this unique pathway of diacylglycerol production may provide a selective mechanism for insulin's regulation of protein kinase C activity, and perhaps explain why phorbol esters reproduce some but not all of the effects of insulin. The further characterization of the molecular components involved in this process, as well as the chemical identities of the aqueous products, may elucidate many of the molecular mechanisms of insulin action.

What is claimed is:

1. A method for treating pathological states of insulin resistance in mammals in need of such therapy, comprising administering a physiologically effective amount of an insulin activity messenger material.

2. A pharmaceutical composition for the treatment of pathological states of insulin resistance in humans in need of such therapy, comprising:

A. pharmaceutically effective amount of an insulin activity messenger material; and
B. a pharmaceutically effective carrier.

3. A pharmaceutical composition for the treatment of pathological states of altered metabolism in humans in need of such therapy, comprising:

A. pharmaceutically effective amount of an antibody to insulin activity messenger material; and
B. a pharmaceutically effective carrier.

* * * * *

UNITED STATES PATENT AND TRADEMARK OFFICE
CERTIFICATE OF CORRECTION

PATENT NO. : 4,906,468
DATED : MARCH 6, 1990
INVENTOR(S) : ALAN R. SALTIEL

It is certified that error appears in the above-identified patent and that said Letters Patent is hereby corrected as shown below:

IN THE TITLE OF THE INVENTION, CHANGE TITLE TO READ:

INSULIN ACTIVITY MESSENGERS, THEIR ANTIBODIES, AND USES THEREOF

Signed and Sealed this

Nineteenth Day of February, 1991

Attest:

HARRY F. MANBECK, JR.

*Attesting Officer*     *Commissioner of Patents and Trademarks*